US010527630B2

(12) United States Patent
Bestard Matamoros et al.

(10) Patent No.: US 10,527,630 B2
(45) Date of Patent: Jan. 7, 2020

(54) METHOD FOR DETECTING ANTIBODY-SECRETING B CELLS SPECIFIC FOR HLA

(71) Applicant: Institut D'Investigació Biomèdica de Bellvitge (IDIBELL), Hospitalet de Llobregat (ES)

(72) Inventors: Oriol Bestard Matamoros, Barcelona (ES); Marc Lúcia Perrez, Barcelona (ES); Josep Maria Grinyó Boira, Castelldefels (ES); Josep Maria Cruzado Garrit, Barcelona (ES); Joan Torras Ambros, Barcelona (ES)

(73) Assignee: Institut D'Investigació Biomèdica de Bellvitge (IDIBELL), Hospitalet de Llobregat (ES)

( * ) Notice: Subject to any disclaimer, the term of this patent is extended or adjusted under 35 U.S.C. 154(b) by 331 days.

(21) Appl. No.: 15/315,053

(22) PCT Filed: Jun. 4, 2015

(86) PCT No.: PCT/EP2015/062517
§ 371 (c)(1),
(2) Date: Nov. 30, 2016

(87) PCT Pub. No.: WO2015/185697
PCT Pub. Date: Dec. 10, 2015

(65) Prior Publication Data
US 2017/0089919 A1 Mar. 30, 2017

(30) Foreign Application Priority Data
Jun. 4, 2014 (EP) .................................... 14382214

(51) Int. Cl.
G01N 33/68 (2006.01)
G01N 33/50 (2006.01)
G01N 33/564 (2006.01)
G01N 33/569 (2006.01)

(52) U.S. Cl.
CPC ..... *G01N 33/6854* (2013.01); *G01N 33/5052* (2013.01); *G01N 33/564* (2013.01); *G01N 33/56977* (2013.01); *G01N 2800/24* (2013.01); *G01N 2800/245* (2013.01); *G01N 2800/50* (2013.01)

(58) Field of Classification Search
None
See application file for complete search history.

(56) References Cited

U.S. PATENT DOCUMENTS 5,856,462 A 1/1999 Agrawal

FOREIGN PATENT DOCUMENTS

| WO | WO-96/02555 A1 | 2/1996 |
| WO | WO-99/33488 A2 | 7/1999 |
| WO | WO-02/085905 A1 | 10/2002 |
| WO | WO-2003/043572 A2 | 5/2003 |
| WO | WO-2004/071459 A2 | 8/2004 |

OTHER PUBLICATIONS

Chia et al. (Tissue Antigens 1991 37: 49-55) (Year: 1991).*
Paantjens et al. (Pulmonary Medicine 2011, 9 pages total). (Year: 2011).*
Susal et al. Human Immunology vol. 65, p. 810-816 (Year: 2004).*
Otten et al. (Am. J. Transplantation 2012 vol. 12, p. 1618-1623). (Year: 2012).*
Tomai et al. (Cellular Immunology 2000 vol. 203, p. 55-65) (Year: 2000).*
US 6,008,200, Dec. 28, 1999, University of Iowa Research Foundation (withdrawn).
Claas, F.H.J. and Doxiadis, I.I.N., Management of the highly sensitized patient, Current Opinion in Immunology, 21:569-572 (2009).
Gebel, H.M. et al., Pre-Transplant Assessment of Donor-Reactive, HLA-Specific Antibodies in Renal Transplantation: Contraindication vs. Risk, American Journal of Transplantation, 3:1488-1500 (2003).
Heidt, S. et al., A Novel ELISPOT Assay to Quantify HLA-Specific B Cells in HLA-Immunized Individuals, American Journal of Transplantation, 12:1469-1478 (2012).
International Search Report for PCT/EP2015/062517, 3 pages, dated Feb. 9, 2015.
Jahnmatz, M. et al., Optimization of a human IgG B-cell ELISpot assay for the analysis of vaccine-induced B-cell responses, Journal of Immunological Methods, 391:50-59 (2013).
Lefaucheur, C. et al., Preexisting Donor-Specific HLA Antibodies Predict Outcome in Kidney Transplantation, J Am Soc Nephrol, 21:1398-1406 (2010).
Massilamany, C. et al., Detection of autoreactive CD4 T cells using major histocompatibility complex class II dextramers, BMC Immunology, 12:40 (2011).
Mulder, A. et al., Determination of the frequency of HLA antibody secreting B-lymphocytes in alloantigen sensitized individuals, Clin Exp Immunol, 124:9-15 (2001).
Mulder, A. et al., Indentification, Isolation, and Culture of HLA-A2-Specific B Lymphocites Using MHC Class I Tetramers, The Journal of Immunology, 171:6599-6603 (2003).

(Continued)

*Primary Examiner* — Changhwa J Cheu
(74) *Attorney, Agent, or Firm* — Choate Hall & Stewart LLP; Charles E. Lyon; Brian E. Reese

(57) ABSTRACT

The invention relates methods for detecting antibody-secreting B-cells specific for at least an HLA in a subject. The invention also relates to kits for developing said methods and to the use of said methods for determining the risk of a subject having humoral rejection against an allogeneic transplant, for determining the risk of a subject of suffering endarteritis associated with post-transplant humoral rejection after allogeneic organ or tissue transplant, for selecting a subject to receive a transplant, and for determining the presence of humoral sensitization against HLA.

19 Claims, 21 Drawing Sheets

(56) References Cited

OTHER PUBLICATIONS

Panoskaltsis-Mortari, A. et al., In situ identification of allospecific B cells using pentamers, Blood, 111:3904-3905 (2008).
Written Opinion for PCT/EP2015/062517, 8 pages, dated Feb. 9, 2015.
Zachary, A.A. et al., HLA-Specific B Cells I: A Method for Their Detection, Quantification, and Isolation Using HLA Tetramers, Transplantation, 83(7):982-988 (2007).
Zachary, A.A. et al., HLA-Specific B Cells II: Application to Transplantation, Transplantation, 83(7):989-994 (2007).

* cited by examiner

A

B

A

B

A $$\text{HLA-specific IgG-ASC frequency} = \frac{\text{HLA-specific spot number}}{\text{Total Polyconal IgG spot number}}$$

B

|  | HLA Antigen | Total IgG-spots | | HLA-spots | | HLAsp/IgGpoly ratio | MFI |
|---|---|---|---|---|---|---|---|
| P#1 | A11:01 | 124 | | 33 | | 0.265 | 12565 |
| | A2:01 | 124 | | 47 | | 0.382 | 15169 |
| | A24 | 124 | | 42 | | 0.337 | 14784 |
| P#2 | A11:01 | 209 | | 92 | | 0.440 | 1858 |
| | A2:01 | 209 | | 37 | | 0.179 | 9080 |
| | A24 | 209 | | 120 | | 0.574 | 2359 |

ROC Curve

Diagonal segments are produced by ties.

| Area | Std. Error[a] | Asymptotic Sig.[b] | Asymptotic 95% Confidence Interval | |
|---|---|---|---|---|
| | | | Lower Bound | Upper Bound |
| ,893 | ,088 | ,011 | ,721 | 1,000 |

Coordinates of the Curve

Test Result Variable(s): ds_BCE_ratio

| Positive if Greater Than or Equal To[a] | Sensitivity | 1 – Specificity |
|---|---|---|
| ,0000 | 1,000 | 1,000 |
| ,0550 | 1,000 | ,875 |
| ,0950 | 1,000 | ,750 |
| ,1250 | 1,000 | ,625 |
| ,1600 | 1,000 | ,500 |
| ,2200 | 1,000 | ,375 |
| ,2850 | 1,000 | ,250 |
| ,3500 | ,857 | ,250 |
| ,4250 | ,714 | ,125 |
| ,4850 | ,571 | ,125 |
| ,5850 | ,429 | ,125 |
| ,6750 | ,286 | ,000 |
| ,8300 | ,143 | ,000 |
| 1,0000 | ,000 | ,000 |

A

B

A

METHOD FOR DETECTING ANTIBODY-SECRETING B CELLS SPECIFIC FOR HLA

CROSS REFERENCE TO RELATED APPLICATIONS

This application is a U.S. National Stage Application filed under 35 U.S.C. § 371 based on International Application No. PCT/EP2015/062517, filed Jun. 4, 2015, which claims priority to European patent application No. 14382214.6, filed Jun. 4, 2014, the entire contents of each of which are hereby incorporated herein by reference.

FIELD OF THE INVENTION

The present invention relates methods for detecting antibody-secreting B-cells specific for HLA in a subject and to the use of said methods for determining the risk of a subject having humoral rejection against an allogeneic transplant, for selecting a subject to receive a transplant and for determining the presence of humoral sensitization against HLA.

BACKGROUND OF THE INVENTION

Humoral rejection is the most challenging immunological barrier to overcome in allotransplantation in humans. Currently, either in its acute or chronic forms of clinical presentation, it accounts for one of the most prevalent etiology of kidney allograft loss. Moreover, today up to almost 40 percent of patients in the waiting list for receiving a kidney transplant are considered as allosensitized, that is, with detectable presence of circulating antibodies against HLA antigens in peripheral blood. As a consequence, the accurate detection of donor-specific antibodies (DSA) has allowed transplant physicians an optimal prevention of early post-transplant antibody-mediated rejection in terms of establishing preventive therapeutic strategies and also even precluding patients undergoing transplantation due to the excessive rejection risk.

Two major B-cell populations that contribute to the maintenance of immunological memory are long-lived plasma cells and memory B cells. The long-lived plasma cells reside primarily in the bone marrow and continuously secrete antibodies that act rapidly on invading microbes. Memory B cells reside primarily in peripheral lymphoid tissues and can, upon re-encounter with the priming antigen, differentiate into antibody-secreting cells (ASC) and thus amplify the antibody response During a sensitization process such as transplantation, the body produces both long-lived plasma cells and memory B cells that provide an immunological memory. Conventionally, in the transplant setting B-cell responses are assessed by the serological measurement of specific antibodies against donor-antigens (DSA). In fact, there are many immune assays evaluating donor-specific circulating HLA antibodies such as complement dependent cytotoxicity (CDC), ELISA, flow cytometry or Luminex-based assays. However, although these assays are valuable for determination of DSA in the circulation, they are likely to underestimate the magnitude of the humoral immune response as it excludes the detection of the memory B-cell pool. In fact, memory B cells can exist in the absence of detectable serum antibody levels and their rapid differentiation and antibody production may be of high relevance for a protective humoral response.

In fact, there are different pathological situations in the kidney transplant setting in which circulating anti-donor HLA antibodies cannot be found using highly sensitive assays despite strong clinical evidence of humoral allosensitization, for instance in patients on the waiting list for a subsequent kidney transplant and not showing circulating antibodies against HLA antigens against previous graft alloantigens, or in kidney transplant recipients showing hystopathological features of antibody-mediated damage but without any evidence of DSA in peripheral blood. Indeed, these features may be apparent due to the eventual absorption of antigen-specific antibodies by the HLA mismatch graft or because of low antigen immunogenicity of donor antigens triggering transient low B-cell stimulation, thus leading to undetectable antibody release. Noteworthy, these biological conditions have relevant clinical implications since an individual considered non-sensitized by means of detectable circulating alloantibodies, could indeed display a very robust antigen-specific memory B-cell response, ready to generate a strong secondary immune response in case of a subsequent exposure to a previously recognized HLA-antigen. Therefore, detecting and quantifying memory B cells capable of producing donor-directed anti-HLA antibodies at different time points of the transplant setting (both before and after) would significantly refine current immune-monitoring tools of the effector alloimmune response.

In this regard relevant clinical situations in which such assay would provide outstanding information from the clinical perspective could be enumerated as follows: (a) before the transplant surgery to demonstrate lack of allosensitization in patients awaiting for a first or subsequent allograft with or without circulating anti-HLA antibodies, (b) before transplantation in well-known sensitized individuals in which specificity and degree of sensitization (MFI or mean fluorescence intensity) varies while being on the waiting list, (c) in sensitized patients undergoing desensitization programs in order to prove a significant inhibition not only of circulating DSA but also of the frequency of donor-specific ASC after treatment and furthermore, (d) after kidney transplantation in patients showing critical histological lesions highly suggestive of antibody-mediated damage but without any evidence of anti-HLA antibodies circulating in peripheral blood.

So far, reproducible assays aiming to quantify the number of cells contributing to alloantibody production are scarce. A HLA-tetramer staining of CD19+ B cells has been reported (Mulder et al., J. Immunol. 2003, 171: 6599-6603) and further developed by Zachary et al. (Zachary et al., Transplantation 2007, 83: 982-988; Zachary et al., Transplantation 2007, 83: 989-994) for the detection and enumeration of B cells which harbor a HLA-specific B-cell receptor, but per se this technique does not quantify B cells that are actually capable of antibody production. More recently, a previously described technique to estimate the precursor frequency of B cells with HLA specificity was based on a CD40L-driven B-cell culture stimulation method including standardized supplements and B-cell sorted responder cells, followed by a visualization phase in ELISPOT format with synthetic HLA molecules as the detection matrix (Mulder et al., Clin. Exp. Immunol. 2001, 124: 9-15; Heidt et al., A. Am. J. Transplant. 2012, 112(6): 1469-78). However, this approach renders it not feasible to standardization as would be required for a clinical test.

Therefore, there is still a need in the art for a reliable and reproducible method for determining and quantifying B cells that are actually capable of producing antibodies directed to HLA.

SUMMARY OF THE INVENTION

The inventors of the present invention have developed a system for detecting and quantifying memory B cells which are able to produce and secrete antibodies specific for HLA. In particular, the inventors have developed a novel B-cell ELISPOT assay that allows the determination of the frequency of HLA-specific antibody-producing memory B cells (example 1). Using this assay, individuals identified as highly sensitized against multiple HLA-specific antigens by determination of HLA-specific antibodies in peripheral blood also exhibit high-frequency of HLA-specific ASC (FIGS. 1 and 2). Interestingly, this assay identifies patients that, in spite of having no evidence of donor-specific antibodies by LUMINEX before transplantation, do have high frequency of donor-specific ASC, and eventually experience antibody-mediated rejection (ABMR) after transplantation (FIG. 5). The assay also allows detection of HLA-specific ASC in patients on the waiting list for a subsequent kidney allograft, even if these patients do not show circulating HLA-specific antibodies against HLA-mismatch antigens of the previous graft (FIG. 4).

Based on the previous findings, the following inventive aspects have been developed.

In a first aspect, the invention relates to an in vitro method for detecting antibody-secreting B cells specific for at least an HLA in a subject comprising:

i) stimulating memory B cells in a sample containing memory B cells from said subject, ii) capturing the antibodies secreted by the stimulated memory B cell of step (i) with an antibody specific to IgG or IgM, iii) contacting the antibodies captured in step (ii) with at least an HLA multimer of said HLA and iv) detecting the HLA multimer of said HLA bound to the antibodies captured in step (ii).

In a second aspect, the invention relates to an in vitro method for determining the risk of a subject of having humoral rejection after allogeneic organ or tissue transplant comprising detecting in a sample from said subject the levels of antibody-secreting B cells specific for at least an HLA using the method of the first aspect, wherein said HLA is present in the transplanted organ or tissue or in the organ or tissue to be transplanted and wherein increased levels of antibody-secreting B cells specific for said HLA in relation to a reference value are indicative of said subject having a high risk of humoral rejection.

In a third aspect, the invention relates to an in vitro method for determining the risk of a subject of suffering endarteritis associated with post-transplant humoral rejection after allogeneic organ or tissue transplant, comprising detecting in a sample from said subject the levels of antibody-secreting B cells specific for at least an HLA using the method of the first aspect, wherein said HLA is present in the transplanted organ or tissue or in the organ or tissue to be transplanted and wherein increased levels of antibody-secreting B cells specific for said HLA in relation to a reference value are indicative of said subject having a high risk of suffering endarteritis associated with post-transplant humoral rejection.

In a fourth aspect, the invention relates to an in vitro method for selecting a subject to receive an allogeneic organ or tissue transplant comprising detecting in a sample from said subject the levels of antibody-secreting B cells specific for at least an HLA using the method of the first aspect, wherein said HLA is present in the organ or tissue to be transplanted and wherein the subject is selected to receive said allogeneic organ or tissue transplant if decreased levels of antibody-secreting B cells specific for said HLA in relation to a reference value are detected.

In a fifth aspect, the invention relates to an in vitro method for determining the presence of humoral sensitization against at least an HLA in a subject comprising detecting the levels of antibody-secreting B-cells specific for said HLA using the method of the first aspect, wherein the detection of an antibody-secreting B-cell specific for said HLA is indicative of said subject having a humoral sensitization against said HLA.

In a sixth aspect, the invention relates to a kit for detecting antibody-secreting B-cells specific for said HLA in a sample comprising B cells comprising an antibody specific to IgG or IgM and at least one HLA multimer.

DETAILED DESCRIPTION OF THE INVENTION

Figure 1:
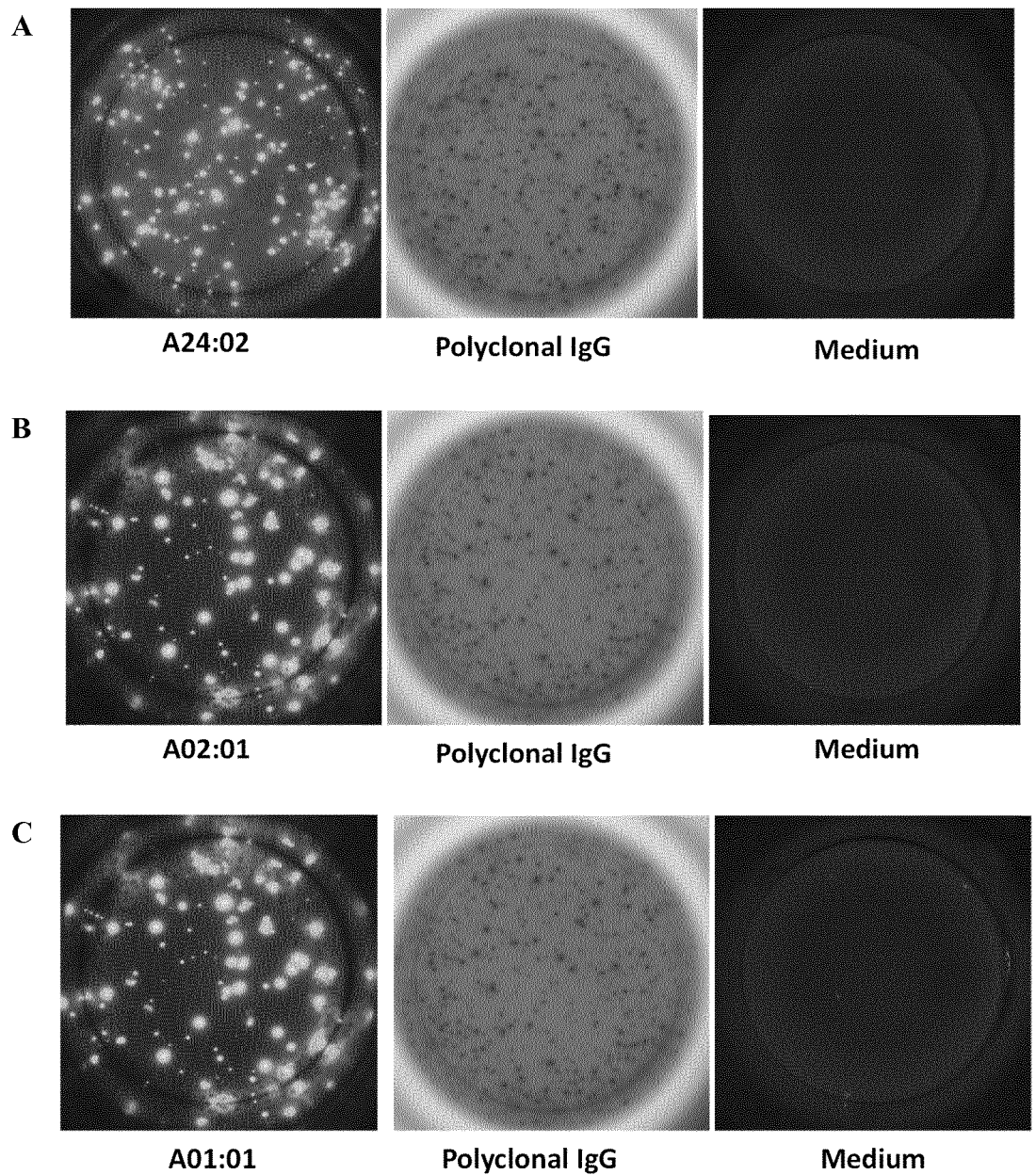
FIG. 1. Representative HLA-specific wells using the B-cell ELISPOT assay of 3 different sensitized patients. (a) First patient showing high number of IgG spots against A24:02, a polyclonal IgG response and a negative control against medium alone. (b) A second individual tested against A2:01, the polyclonal IgG secretion and medium. (c) A third sensitized transplant patient against A11:01, medium and polyclonal IgG secretion.

Method for detecting antibody-secreting B cells specific for an HLA In a first aspect, the invention relates to an in vitro method for detecting antibody-secreting B cells specific for at least an HLA in a subject, hereinafter first method of the invention, comprising:

i) stimulating memory B cells in a sample containing memory B cells from said subject, ii) capturing the antibodies secreted by the stimulated memory B cell of step (i) with an antibody specific to IgG or IgM, iii) contacting the antibodies captured in step (ii) with at least an HLA multimer of said HLA and iv) detecting the HLA multimer of said HLA-bound to the antibodies captured in step (ii).

The term "B cell", as used herein, refers to a type of lymphocyte that plays a major role in the humoral immune response, as opposed to the cell-mediated immune response, which is governed by T cells. B cells are characterized by the presence of a B cell receptor (BCR) on their outer surface which allows the B cell to bind to its specific antigen. The principal functions of a B cell are (i) to produce antibodies against the specific antigens which it recognizes, (ii) to perform the role of antigen-presenting cells (APCs) and (iii) to eventually develop into memory B cells after activation by interacting with its cognate antigen. B cells are an essential component of the adaptive immune system. The term "B cell" includes long-lived plasma cells and memory B cells. The term "long-lived plasma B cell", as used herein, refers to a sub-type of B cells that reside primarily in the bone marrow and continuously secrete antibodies. The term "memory B cell", as used herein, refers to a sub-type of B cells that are formed following a primary infection and activation by interacting with its cognate antigen, reside primarily in peripheral lymphoid tissues and, upon re-encounter with the priming antigen, differentiate into antibody-secreting cells (ASC) thus amplifying the antibody response. In a preferred embodiment, the B cell is a memory B cell.

The first method of the invention detects antibody-secreting B cells, i.e., B cells which are capable of producing and secreting antibodies.

The term "HLA" or "human leukocyte antigen", as used herein, refers to the major histocompatibility antigens (MHC) of humans, which are encoded by the genes found on the locus that forms the HLA system. The MHC is a set of cell surface molecules encoded by a large gene family in vertebrates. MHC molecules display on the cell surface a fraction of a protein or epitope, which can be either of the host's own phenotype or of other biological entities.

The HLA system is the name of the locus of genes that encode for said HLA antigens in humans. The super-locus contains a large number of genes related to immune system function in humans. This group of genes, which resides on chromosome 6, encodes cell-surface antigen-presenting proteins and has many other functions.

In a preferred embodiment, the HLA corresponds to MHC class I. In another embodiment, the HLAs correspond to MHC class II. In another embodiment, the HLA belongs to the HLA-A, HLA-B, HLA-C, HLA-E, HLA-F, HLA-G, HLA-H, HLA-J, HLA-K, HLA-L, HLA-P, HLA-V, HLA-DRA, HLA-DRB1, HLA-DRB2-9, HLA-DQA1, HLA-DQB1, HLA-DPA1, HLA-DPB1, HLA-DMA, HLA-DMB, HLA-DOA, HLA-DOB, MICA, MICB, TAP1, TAP2, and/or KIR type.

The method according to the invention allows the detection of cells capable of expressing any HLA-specific antibody as long as the HLA is known and the corresponding HLA can be provided in multimeric form. Suitable cells that can be detected using the method of the invention include cells that produce antibodies specific for any of the HLA which are described in the web page hla.alleles.org.

HLA system is highly polymorphic, there being many alleles at each individual locus.

In a transplant procedure, HLA molecules act themselves as antigens and can provoke an immune response in the recipient, resulting in a transplant rejection. Each human cell expresses six MHC class I alleles (one HLA-A, -B, and -C allele from each parent) and six to eight MHC class 2 alleles (one HLA-DP and -DQ, and one or two HLA-DR from each parent, and combinations of these). The HLA variation in the human population is high, at least 350 alleles for HLA-A genes, 620 alleles for HLA-B, 400 alleles for DR, and 90 alleles for DQ. Any two individuals who are not identical twins will express differing HLA molecules. All HLA molecules can mediate transplant rejection, but HLA-C and HLA-DP, showing low polymorphism, seem least important. In a transplant procedure, HLA molecules act themselves as antigens and can provoke an immune response in the recipient, resulting in a transplant rejection.

The term "antibody-secreting B cells specific for at least one HLA", as used herein, refers to a B cell, which is secreting an antibody that specifically binds one HLA, i.e., an antibody that binds to one HLA and displays substantially no binding to other HLA unless they share the same antigenic determinants.

The term "subject", as used herein, refers to all human beings, male or female, of any age or race.

The method of the first aspect comprises the following steps.

(i) Stimulating Memory B Cells in a Sample Containing Memory B Cells from Said Subject The term "sample containing memory B cells", as used herein, refers to any sample derived from the subject which contains memory B cells, for example, a biological fluid like blood, plasma, serum or lymph or a cell, tissue, organ or portion thereof containing memory B cells like bone marrow, spleen or lymph nodes. In a particular embodiment, the sample containing memory B cells is a peripheral blood sample, preferably a peripheral blood sample containing peripheral blood mononuclear cells (PBMCs). The term "peripheral blood" relates to the blood volume that circulates distant of the heart, that is, blood flowing through the body of a subject. The blood sample can be obtained by conventional methods known to those skilled in the art. The term "peripheral blood mononuclear cell" or "PBMC" refers to any blood cell having a round nucleus (as opposed to a lobed nucleus), such as a lymphocyte, a monocyte or a macrophage. PBMCs can be extracted from whole blood using methods that are well known in the art. In another particular embodiment, the sample containing memory B cells is a sample containing purified B cells. B cells can be purified from whole blood by means of methods that are conventional for the skilled person, such as for example the method described in Heidt et al., 2012 (cited supra).

The term "stimulating", as used herein, refers to inducing the differentiation of the memory B cell into an antibody-secreting cell (ASC). The terms stimulating a memory B cell and activating a memory B cell are used indistinctly in the context of the invention.

The skilled person knows how to stimulate a memory B cell in order to induce its differentiation into an ASC. For example, a memory B cell can be stimulated and differentiated into an ASC by incubating the sample containing memory B cells in the presence of IL-2 and a TLR agonist, or alternatively, by incubating the sample containing memory B cells in the presence of IL-2 and an anti-CD40 antibody.

The term "IL-2" or "interleukin 2", as used herein, refers to a protein which is a member of a cytokine family that also includes IL-4, IL-7, IL-9, IL1-5 AND IL-21. The IL-2 can be from any origin, for example human, bovine, murine, equine, canine, etc. In a preferred embodiment, the IL-2 is the human protein with the UniProt accession number P60568 (14 May 2014). The IL-2 can be isolated from a natural source or produced by synthetic or recombinant methods.

The term "TLR agonist", as used herein, refers to a molecule which is capable of causing a signaling response through a TLR signaling pathway, either as a direct ligand or indirectly through generation of endogenous or exogenous. Agonistic ligands of TLR receptors are (i) natural ligands of the actual TLR receptor, or functionally equivalent variants thereof which conserve the capacity to bind to the TLR receptor and induce co-stimulation signals thereon, or (ii) an agonist antibody against the TLR receptor, or a functionally equivalent variant thereof capable of specifically binding to the TLR receptor and, more particularly, to the extracellular domain of said receptor, and inducing some of the immune signals controlled by this receptor and associated proteins. The binding specificity can be for the human TLR receptor or for a TLR receptor homologous to the human one of a different species.

The term "toll-like receptors" or "TLR" refers to a family of type I transmembrane proteins forming part of the innate immune system. In vertebrates they also enable the adaptation of the immune system. TLRs together with interleukin receptors form a superfamily known as the Interleukin-1/toll-like receptor superfamily. All the members of this family have in common the domain called the Toll-IL-1 receptor (TIL) domain.

Any agonist of a TLR can be used in the first method of the invention together with IL-2 for stimulating the memory B cells. Examples of TLR agonists that can be used in the step (i) of the first method of the invention include:

TLR-1 agonists. Non-limiting examples of TLR-1 agonists include tri-acylated lipopeptides (LPs); phenol-soluble modulins; *Mycobacterium tuberculosis* LP; S-(2,3-bis(palmitoyloxy)-(2-RS)-propy 1)-N-palmitoyl-I-Cys-(S)-Ser-(S)-Lys(4)-OH, trihydrochloride (Pam3Cys) LP which simulates the acetylated amino terminus of a bacterial lipoprotein and OspA LP from *Borrelia burgdorferi*.

TLR-2 agonists. Non-limiting examples of TLR-2 agonists include, without limitation, one or more of a bacterial lipopeptide from *M. tuberculosis, B. burgdorferi, T. pallidum*; peptidoglycans from species including *Staphylococcus aureus*; lipoteichoic acids, mannuronic acids, *Neisseria* porins, bacterial fimbriae, *Yersina* virulence factors, CMV virions, measles haemagglutinin, and zymosan from yeast.

TLR-3 agonists, such as double stranded RNA, or polyinosinic-polycytidylic acid (Poly I:C).

TLR-4 agonists, such as the lipopolysaccharide (LPS) from gram-negative bacteria, or fragments thereof; heat shock protein (HSP) 10, 60, 65, 70, 75 or 90; surfactant Protein A, hyaluronic acid oligosaccharides, heparan sulphate fragments, fibronectin fragments, fibrinogen peptides and b-defensin-2.

TLR-5 agonists like, flagelin or a functionally equivalent variant thereof. Suitable flagelins for use according to the present invention include the flagellin encoded by the fljB gene from *Salmonella enterica* serovar Typhymurium LT2 as well as any flagellin *Salmonella enterica* strains that are known and are publicly available on GenBank.

TLR-6 agonists such as mycobacterial lipoprotein, diacylated LP, and phenol-soluble modulin. Further TLR6 agonists are described in WO2003043572.

TLR7 agonists such like resiquimod (R848), loxoribine, a guanosine analogue at positions N7 and C8, or an imidazoquinoline compound, or derivative thereof. In one embodiment, the TLR agonist is imiquimod. Further TLR7 agonists are described in WO02085905.

TLR-8 agonists like resiquimod (R848) or those described in the document WO2004071459.

TLR-9 agonists such as a DNA that contains unmethylated CpG nucleotides, in particular sequence contexts known as CpG motifs. CpG-containing oligonucleotides induce a predominantly Th1 response. Such oligonucleotides are well known and are described, for example, in WO 96/02555, WO 99/33488 and U.S. Pat. Nos. 6,008,200 and 5,856,462.

TLR-10 agonists.

TLR agonist that are capable of causing a signaling response through any combination of two or more of the above TLRs, for example, an agonist of TLR-7 and TLR-8 (TLR7/8 agonist) like resiquimod (R848).

In a preferred embodiment, the TLR agonist is a TLR-7/8 agonist. In a more preferred embodiment, the TLR-7/8 agonist is R848.

The term "resiquimod" or "R848", as used herein, refers to an imidazoquinoline compound with the formula:

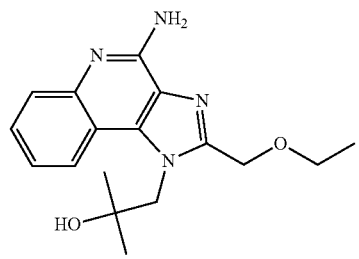 [SMILES: CCOCc1nc2c(N)nc3ccccc3c2n1CC(C)(C)O]

R848 is an agonist of both TLR-7 and TLR-8.

The term "CD40" relates to a costimulatory protein found on antigen presenting cells (APCs), such as B cells, which is required for their activation. The binding of CD154 (CD40L) on TH cells to CD40 activates APCs and induces a variety of downstream effects. Similarly, the activation of APCs can be achieved with the binding of an anti-CD40 antibody, preferably an agonistic anti-CD40 antibody. Methods to evaluate whether an anti-CD40 antibody is agonistic are well-known by the person skilled in the art, and include methods to stimulate B cell proliferation in the presence of IL-4 or IL-2 in a dose-dependent manner, as measured by for example, reagents suitable to measure cell viability and/or metabolic activity, such as resazurin.

(ii) Capturing the Antibodies Secreted by the Stimulated Memory B Cell of Step (i) with an Antibody Specific to IgG or IgM The step of capturing the antibodies secreted by the stimulated B cell is performed by incubating the stimulated B cells of step (i) with an antibody specific to IgG or IgM, i.e. a capturing antibody.

The term "antibody", as used herein, relates to immunoglobulin molecules and immunologically active portions of immunoglobulin molecules, i.e., molecules containing an antigen binding site, which specifically bind (immunoreact) with an antigen, such as, for example, a protein. Antibodies according to the invention include any agent capable of binding to a ligand with high affinity, including IgG, IgM, IgA, IgD and IgE, as well as antibody fragments or antibody constructs which have an antigen binding site, such as Fab', Fab, F(ab')2, single domain antibodies or DABS, Fv, scFv and the like, also known as "antigen binding fragments of an antibody". The antibody can be a polyclonal or a monoclonal antibody. The antibody can also be of any origin, including, without limitation, murine antibodies, human antibodies, shark antibodies, and camelid antibodies. When the antibody is not of human origin, it can be chimeric or humanized. The techniques for preparing said antibodies are very well-known for the person skilled in the art.

The term "antibody specific to IgG or IgM" or "capturing antibody", as used herein, refers to an antibody that specifically binds to the constant region of the heavy chain, which is identical in all the antibodies of the same isotype, of an IgG antibody or of an IgM antibody.

The term "immunoglobulin G" or "IgG", as used herein, refers to an antibody isotype of about 150 kDa composed of four peptide chains. It contains two identical class y heavy chains of about 50 kDa and two identical light chains of about 25 kDa, thus a tetrameric quaternary structure. The two heavy chains are linked to each other and to a light chain each by disulfide bonds. The resulting tetramer has two identical halves, which together form a Y-like shape. Each end of the fork contains an identical antigen binding site. The Fc regions of IgG bear a highly conserved N-glycosylation site. The N-glycans attached to this site are predominantly core-fucosylated diantennary structures of the complex type. In addition, small amounts of these N-glycans also bear bisecting GlcNAc and $\alpha$-2,6-linked sialic acid residues.

The term "immunoglobulin M" or "IgM", as used herein, refers to an antibody isotype of about 970 Kda composed of multiple immunoglobulins covalently linked together by disulfide bonds forming a pentamer or a hexamer, although it can also exists as a monomer. Each monomer consists of four peptide chains, two identical p heavy chains and two identical light chains. In the pentameric form, IgM has a J chain covalently bound via disulfide bonds which functions in polymerization of the molecule into a pentamer.

In a particular embodiment, the capturing antibody is immobilized onto a solid surface, for example, a microwell or multiwell plate. The solid surface is preferably made of polyvinylidene difluoride (PVDF). In this particular embodiment, it is possible to add the stimulated B cells of step (i), more specifically the sample containing stimulated B cells resulting from step (i) onto a surface, for example a plate, more specifically a PVDF plate, pre-coated with the antibody specific to IgG or IgM.

As the skilled person knows, in order to capture the antibodies secreted by the stimulated B cell, i.e., in order to allow the binding of the antibodies secreted by the stimulated B cell to the antibody specific for IgG or IgM, the contacting between both types of antibodies should be performed under conditions appropriate for said binding. The skilled person will be able to determine which conditions (temperature, time of incubation, etc.) are the most appropriated for capturing the secreted antibodies. In a particular embodiment, the capturing is performed by incubating the sample containing the stimulated B cells into a plate pre-coated with the antibody specific to IgG or IgM into a 37° C. incubator for 24 hours.

In another embodiment, once the antibodies secreted by the stimulated B cell have been contacted with the antibody specific for IgG or IgM, the mixture can be washed one or more times in order to remove non-specifically bound antibodies that might influence the read-out.

(iii) Contacting the Antibodies Captured in Step (ii) with at Least an HLA Multimer of Said HLA The step of contacting the antibodies captured in step (ii) with at least an HLA multimer of said HLA for which specific antibody-secreting B cells are to be detected is done by incubating said captured antibodies with at least an HLA multimer of said HLA.

The term "HLA multimer", as used herein, refers to an oligomeric form of an HLA molecule. HLA multimers comprise a backbone to which HLA monomers are bound, creating a multimeric structure. Illustrative non limitative examples of HLA multimers include HLA multimers comprising at least 2, or at least 3, or at least 4, or at least 5, or at least 6, or at least 7, or at least 8, or at least 9, or at least 10, or at least 11, or at least 12 HLA molecules, preferably between 4 to 12 HLA molecules, more preferably between 5 and 10 HLA molecules, even more preferably between 6 and 9 HLA molecules. It will be understood that the HLA molecules need not be the same or of the same type in the HLA multimer. In a particular embodiment, the HLA multimer is a HLA dextramer, which comprise HLA molecules attached to a dextran backbone.

In a particular embodiment, the HLA multimer is a polymeric molecule to which a plurality of molecules of said HLA is attached.

The term "polymeric molecule", as used herein, refers to a chemical compound or mixture of compounds consisting of repeating structural units created only through a process of polymerization. The polymeric molecule can contain only a single type of repeat unit (homopolymers), or a mixture of repeat units (heteropolymers or copolymers). Any polymeric molecule to which multiple HLA molecules can be bound can form part of the HLA multimer according to the method of the first aspect. In a particular embodiment, the polymeric molecule is dextran.

The term "dextran", as used herein, refers to a complex, branched glucan composed of chains of varying lengths (from 3 to 2000 Kda). The straight chain consists glucose molecules bound by $\alpha$-1,6 glycosidic linkages, while branches begin from $\alpha$-1,3 linkages.

In another particular embodiment, a label is attached to the HLA multimer.

Optionally, HLA multimers containing more than one type of HLA molecule may be contacted with the captured antibodies to allow simultaneous detection of antibody-secreting B cells with different HLA specificities.

Thus, in another particular embodiment, the antibodies captured in step (ii) are contacted with at least two HLA multimers, wherein the type of HLA molecules contained in each of said at least two HLA multimer is different. In a preferred embodiment, the antibodies captured in step (ii) are contacted with at least 2, or at least 3, or at least 4, or at least 5, or at least 6, or at least 7, at least 8, at least 9, at least 10 HLA multimers, wherein the type of HLA molecules contained in each of said at least 2, or at least 3, or at least 4, or at least 5, or at least 6, or at least 7, at least 8, at least 9, at least 10 HLA multimers, respectively, is different. When HLA multimers of different HLA specificity are used, they may contain the same or different number of HLA molecules. It will be immediately understood that for certain purposes, such as for quantifying the levels of antibodies binding to HLA of different specificities, it is preferred that the HLA multimers of different HLA specificity contain the same number of HLA molecules.

In a preferred embodiment, a different label is attached to each of the at least two HLA multimers.

The term "label", as used herein, refers to any composition which can be used to detect, qualitatively or quantitatively, a substance attached to the label. Suitable labels include a fluorescent moiety, a radioisotope, a chromophore, a bioluminescent moiety, an enzyme, a magnetic particle, an electron dense particle, and the like. In a particular embodiment, the label is a fluorochrome molecule.

The term "fluorochrome molecule", as used herein, refers to all those compounds which absorb light at a determined wavelength or wavelength range and emit light at a different wavelength or wavelength range. Fluorescent molecules suitable for their use in the present invention include but are not limited to ethidium bromide, SYBR Green, fluorescein isothiocyanate (FITC), phycoerythrin, R-Phycoerythrin, tetramethyl rhodamine isothiol (TRIT), 5-carboxyfluorescein, 6-carboxyfluorescein, fluorescein, HEX (6-carboxy-2', 4,4',5',7,7'-hexachlorofluorescein), Oregon Green 488, Oregon Green 500, Oregon Green 514, Joe (6-carboxy-4', 5'-dichloro-2',7'-dimethoxyfluorescein), 5-carboxy-2',4',5', 7'-tetrachlorofluorescein, 5-carboxyrhodamine, rhodamine, tetramethylrhodamine (Tamra), Rox (carboxy-X-rhodamine), R6G (rhodamine 6G), phthalocyanines, azomethines, cyanines (Cy2, Cy3 and Cy5), Texas Red, Princeton Red, BODIPY FL-Br2, BODIPY 530/550, BODIPY TMR, BODIPY 558/568, BODIPY 564/570, BODIPY 576/589, BODIPY 581/591, BODIPY TR, BODIPY 630/650, BODIPY 650/665, DABCYL, Eosin, Erythrosine, ethidium bromide, green fluorescent protein (GFP) and the analogs thereof, inorganic fluorescent labels based on semiconductor nanocrystals (Quantum dot), fluorescent labels based on lanthanides such as Eu3+ and Sm3+ and the like.

In a preferred embodiment, the fluorochrome molecule is selected from FITC, phycoerythrin and R-Phycoerythrin.

(iv) Detecting the HLA Multimer of Said HLA Bound to the Antibodies Captured in Step (ii)

The step of detecting the HLA multimer bound to the antibodies capture in step (ii) can be performed by any method known by the skilled person appropriate for detecting HLA multimers. The detection process can be incorporated in particular assay formats illustratively including ELISA, western blot, immunoprecipitation, immunocytochemistry, immuno-fluorescence assay, liquid chromatography, flow cytometry, fluorescence-activated cell sorting, other detection techniques known in the art, or combinations thereof. This step may require the use of secondary detecting molecules specific for the HLA multimer, such as antibodies conjugated with a detectable label. This is standard in the art and the skilled person will immediately recognize which secondary detecting molecules are suitable for the purpose of the invention.

In the particular embodiment where a label is attached to the HLA multimer, the detection can be performed by detecting said label. The detecting process will depend on the nature of the label. In a particular embodiment, if the label is a fluorochrome molecule, it can be detected by any method that allows fluorescent determination, for example, a fluorescence reader.

The levels of HLA-specific antibodies may be normalized to the level of total antibodies present in the sample. This allows a more accurate expression of the specific amount and frequency of any HLA-specific antibody-secreting B cells clone over the global polyclonal memory B-cell compartment, which remains stable over time thereby illustrating a higher stability of anti-HLA memory B cells as compared to only measuring circulating anti-HLA antibodies. In this way, the detecting method according to the invention allows the determination of the ratio of HLA-specific antibodies secreting cells to the number of total cell secreting antibodies. The normalization can be carried out by plating a duplicate of the stimulated cell population, capturing the antibodies according to step (ii) of the method of the invention and detecting antibodies using a second antibody which is capable of specifically binding to any antibody which is secreted by the cells captured in step (i).

Method for Determining the Risk of a Subject Having Humoral Rejection after Allogeneic Organ or Tissue Transplant In another aspect, the invention relates to an in vitro method for determining the risk of a subject of having humoral rejection after allogeneic organ or tissue transplant, hereinafter second method of the invention, comprising detecting in a sample from said subject the levels of antibody-secreting B cells specific for at least an HLA using the method of the first aspect, wherein said HLA is present in the transplanted organ or tissue or in the organ or tissue to be transplanted and wherein increased levels of antibody-secreting B cells specific for said HLA in relation to a reference value are indicative of said subject having a high risk of humoral rejection.

The terms "in vitro", "subject", "antibody-secreting B cells" and "sample" have been defined in relation with the first method of the invention. The preferred and particular embodiments of first method of the invention regarding these terms are also included in the second method of the invention.

The term "rejection" or "transplant rejection" is used in the present invention in a context of tissue or organ transplant, and is related to the process by which a transplanted tissue or organ is rejected by the immune system of the recipient, which destroys the transplanted tissue or organ.

The term "humoral rejection" or "antibody-mediated rejection" or "AMR", as used herein, refers to a mechanism or transplant rejection, which is mediated by antibodies. Humoral rejection includes hyperacute rejection (HAR) and is a type of rejection characterized by acute allograft injury that is resistant to potent anti-T cell therapy, by the detection of circulating donor specific antibodies, and the deposition of complement components in the graft. AMR with elevated circulating alloantibodies and complement activation that occurs in 20-30 percent of acute rejection cases has a poorer prognosis than cellular rejection.

The humoral rejection can be acute or chronic.

Acute rejection, with onset 2-60 days after transplantation, is characterized by interstitial vascular endothelial cell swelling, interstitial accumulation of lymphocytes, plasma cells, immunoblasts, macrophages, neutrophils; tubular separation with edema/necrosis of tubular epithelium; swelling and vacuolization of the endothelial cells, vascular edema, bleeding and inflammation, renal tubular necrosis, sclerosed glomeruli, tubular 'thyroidization', creatinine clearance, malaise, fever, HTN, oliguria. The acute rejection occurs to some degree in all transplants, except between identical twins, unless immunosuppression is achieved (usually through drugs). Acute rejection begins as early as one week after transplant, the risk highest in the first three months, though it can occur months to years later. Highly vascular tissues such as kidney or liver often host the earliest signs-particularly at endothelial cells lining blood vessels-though it eventually occurs in roughly 10 to 30% of kidney transplants, and 50 to 60% of liver transplants. Generally, acute rejection can be inhibited or suppressed with immunosuppressive drugs such as rapamycin, cyclosporine A, anti-CD40L monoclonal antibody and the like. In the context of the invention, acute rejection is considered to occur at least 3 days, 4 days, 5 days, 6 days, 7 days, 8 days, 9 days, 10 days, 11 days, 12 days, 13 days, 14 days, 15 days, 1 month, 2 months, 3 months or 6 months after transplantation.

Chronic rejection has a late onset, often more than 60 days after transplantation, and frequently accompanied by acute changes superimposed, increased mesangial cells with myointimal proliferation and crescent formation; mesangioproliferative glomerulonephritis, and interstitial fibrosis; there is in general a poor response to corticosteroids. It occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs. In the context of the invention, chronic rejection is considered to occur months after transplantation. In a preferred embodiment of the invention, chronic rejection is considered to occur at least 2 months, at least 3 months, at least 4 months, at least 5 months or at least 6 months after transplantation.

The term "organ or tissue transplant", as used herein, refers to a surgical procedure by which a tissue or organ is transferred from a donor subject to a recipient subject or from one part of the body to another in the same subject. Transplanted tissues comprise, but are not limited to, bone tissue, tendons, corneal tissue, heart valves, veins and bone marrow. Transplanted organs comprise, but are not limited to, heart, lung, liver, kidney, pancreas and intestine. In a particular embodiment, the transplant is an organ transplant. In a more particular embodiment, the organ transplant is a kidney transplant.

The term "allogeneic organ or tissue transplant" or "allotransplant", as used herein, refers to the transplantation of tissues or organs sourced from a genetically non-identical member of the same species as the recipient. The term "allotransplantable" refers to organs or tissues that are relatively often or routinely transplanted. Examples of allotransplantable organs include heart, lung, liver, pancreas, kidney and intestine.

The term "method for determining the risk", as used herein, refers to a method for determining the probability of a particular event. In the context of the second method of the invention, determining the risk of a subject having humoral rejection after allogeneic organ or tissue transplant refers to determining whether said subject has a high likelihood of having humoral rejection. The term "high risk", as used herein, refers to a significantly high probability of having humoral rejection. In a particular embodiment, a high risk is likelihood of at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, 1000%, and 1500%. In one particular embodiment, a high risk is a likelihood of at least 100%. In other embodiments, a high risk is a likelihood of at least 200%, at least 300%, at least 400%, at least 500%, at least 700%, at least 800%, at least 900% and at least 1000%. Other cut-offs or ranges as deemed suitable by the person skilled in the art to characterize the invention are however also contemplated, and those are also within scope of the present invention.

The second method of the invention comprises determining in a sample from the subject the levels of antibody-secreting B cells specific for at least an HLA which is present in the transplanted organ or tissue or in the organ or tissue to be transplanted using the first method of the invention.

The method of the second aspect can be performed before or after the allogeneic transplantation of the tissue or organ. In a particular embodiment, the risk of having humoral rejection is determined before the allogeneic transplantation of the tissue or organ, i.e. the levels of antibody-secreting B cells specific for at least an HLA which is present in the tissue or organ to be transplanted are determined before the allogeneic transplantation of said tissue or organ. In another particular embodiment, the risk of having humoral rejection is determined after the allogeneic transplantation of the tissue or organ, i.e. the levels of antibody-secreting B cells specific for at least an HLA which is present in the transplanted tissue or organ are determined after the allogeneic transplantation of said tissue or organ.

The term "high levels" applied to the levels of the antibody-secreting B cells specific for at least an HLA refers to any level of said antibody-secreting B cells which is higher than a reference value. The levels of a said antibody-secreting B cells are considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or higher than its reference value.

The term "reference value", as used herein, relates to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested.

The reference value according to the second method of the invention can be obtained from one or more non-transplanted subjects or from one or more transplanted subjects who are known to not suffer rejection (i.e., control subjects).

In a particular embodiment, the second method of the invention further comprises the determination of the ratio of HLA-specific antibodies secreting B cells to the number of total cells secreting antibodies. In this particular embodiment, an increase in said ratio in relation to a reference value is indicative of said subject having a high risk of humoral rejection. The determination of the ratio of HLA-specific antibodies secreting B cells to the number of total cells secreting antibodies has been previously explained in relation with the first method of the invention. In the context of the second method of the invention, the ratio is considered "increased" when said ratio is higher than the reference value. The term "higher" than its reference means that the value of the ratio is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or higher than its reference value. The reference value according to this particular embodiment can be the ratio between HLA-specific antibodies secreting B cells to the number of total cells secreting antibodies obtained from one or more non-transplanted subject or from one or more transplanted subjects who are known to not suffer rejection (i.e., control subjects).

Method for Determining the Risk of a Subject of Suffering Endarteritis Associated with Post-Transplant Humoral Rejection after Allogeneic Organ or Tissue Transplant In another aspect, the invention relates to an in vitro method for determining the risk of a subject of suffering endarteritis associated with post-transplant humoral rejection after allogeneic organ or tissue transplant, comprising detecting in a sample from said subject the levels of antibody-secreting B cells specific for at least an HLA using the method of the first aspect, wherein said HLA is present in the transplanted organ or tissue or in the organ or tissue to be transplanted and wherein increased levels of antibody-secreting B cells specific for said HLA in relation to a reference value are indicative of said subject having a high risk of suffering endarteritis associated with post-transplant humoral rejection.

The terms "method for determining the risk", "in vitro", "subject", "allogeneic organ or tissue transplant", "sample", "antibody-secreting B cells", and "HLA" have been defined in relation with the first and second methods of the invention. The preferred and particular embodiments of first and second methods of the invention regarding these terms are also included in the third method of the invention.

The term "endarteritis" or "obliterating endarteritis" or "obliterating arteritis" relates to a severe proliferating endarteritis, which is an inflammation of the intima or inner lining of an artery that results in an occlusion of the lumen of the artery. Endarteritis can occur due to a variety of medical conditions such as a complication of radiation poisoning, TB, meningitis or syphilis infection, or post-transplant humoral rejection.

In an embodiment, the endarteritis occurs in the transplanted organ or tissue.

The third method of the invention comprises determining in a sample from the subject the levels of antibody-secreting B cells specific for at least an HLA which is present in the transplanted organ or tissue or in the organ or tissue to be transplanted using the first method of the invention.

The method of the third aspect can be performed before or after the allogeneic transplantation of the tissue or organ. In a particular embodiment, the risk of suffering endarteritis associated with post-transplant humoral rejection after allogeneic organ or tissue transplant is determined before the allogeneic transplantation of the tissue or organ, i.e. the levels of antibody-secreting B cells specific for at least an HLA which is present in the tissue or organ to be transplanted are determined before the allogeneic transplantation of said tissue or organ. In another particular embodiment, the risk of suffering endarteritis associated with post-transplant humoral rejection after allogeneic organ or tissue transplant is determined after the allogeneic transplantation of the tissue or organ, i.e. the levels of antibody-secreting B cells specific for at least an HLA which is present in the transplanted tissue or organ are determined after the allogeneic transplantation of said tissue or organ.

The term "high levels" applied to the levels of the antibody-secreting B cells specific for at least an HLA refers to any level of said antibody-secreting B cells which is higher than a reference value. The levels of a said antibody-secreting B cells are considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or higher than its reference value.

The term "reference value", as used herein, relates to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested.

The reference value according to the third method of the invention can be obtained from one or more transplanted subjects who suffer with post-transplant humoral rejection after allogeneic organ or tissue transplant and are known to not present endarteritis, or from one or more transplanted subjects who are known to not suffer rejection (i.e., control subjects).

In a particular embodiment, the third method of the invention further comprises the determination of the ratio of HLA-specific antibodies secreting B cells to the number of total cells secreting antibodies. In this particular embodiment, an increase in said ratio in relation to a reference value is indicative of said subject having a high risk of humoral rejection. The determination of the ratio of HLA-specific antibodies secreting B cells to the number of total cells secreting antibodies has been previously explained in relation with the first method of the invention. In the context of the second method of the invention, the ratio is considered "increased" when said ratio is higher than the reference value. The term "higher" than its reference means that the value of the ratio is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or higher than its reference value. The reference value according to this particular embodiment can be the ratio between HLA-specific antibodies secreting B cells to the number of total cells secreting antibodies obtained from one or more transplanted subjects who are known to not suffer endarteritis associated with post-transplant humoral rejection after allogeneic organ or tissue transplant (i.e., control subjects).

Method for Selecting a Subject to Receive an Allogeneic Organ or Tissue Transplant In another aspect, the invention relates to an in vitro method for selecting a subject to receive an allogeneic organ or tissue transplant, hereinafter third method of the invention, comprising detecting in a sample from said subject the levels of antibody-secreting B cells specific for at least an HLA using the method of the first aspect, wherein said HLA is present in the organ or tissue to be transplanted and wherein the subject is selected to receive said allogeneic organ or tissue transplant if low levels of antibody-secreting B cells specific for at said HLA in relation to a reference value are detected.

The terms "in vitro", "subject", "allogeneic organ or tissue transplant", "sample", "antibody-secreting B cells", "HLA" and "reference value" have been defined in relation with the first and second methods of the invention. The preferred and particular embodiments of first and second methods of the invention regarding these terms are also included in the fourth method of the invention.

The term "method for selecting", as used herein, refers to the action of choosing said subject to receive an allogeneic organ or tissue.

According to the fourth method of the invention a subject is selected to receive an allogeneic organ or tissue transplant if low levels of antibody-secreting B cells specific for at least an HLA which is present in the organ or tissue to be transplanted are detected in a sample from said subject in relation to a reference value are detected.

The term "decreased levels" applied to the levels of the antibody-secreting B cells specific for at least an HLA refers to any level of said antibody-secreting B cells which is lower than a reference value. The levels of a said antibody-secreting B cells are considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or lower than its reference value.

In a particular embodiment, the organ transplant is a kidney transplant.

In a particular embodiment, the fourth method of the invention further comprises the determination of the ratio of HLA-specific antibodies secreting B cells to the number of total cells secreting antibodies. In this particular embodiment, a subject is selected to receive the allogeneic organ or tissue transplant if a decrease in said ratio in relation to a reference value is detected in a sample from said subject. The determination of the ratio of HLA-specific antibodies secreting B cells to the number of total cells secreting antibodies has been previously explained in relation with the first method of the invention. In the context of the fourth method of the invention, the ratio is considered "decreased" when said ratio is lower than the reference value. The ratio is considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or lower than its reference value.

The reference value according to this particular embodiment can be the ratio between HLA-specific antibodies secreting B cells to the number of total cells secreting antibodies obtained from one or more non-transplanted subject or from one or more transplanted subjects who are known to not suffer rejection (i.e., control subjects).

In a particular embodiment, the fourth method of the invention further comprises the determination of the ratio of HLA-specific antibodies secreting B cells to the number of total cells secreting antibodies. In this particular embodiment, an increase in said ratio in relation to a reference value is indicative of said subject having a high risk of humoral rejection. The determination of the ratio of HLA-specific antibodies secreting B cells to the number of total cells secreting antibodies has been previously explained in relation with the first method of the invention. In the context of the second method of the invention, the ratio is considered "increased" when said ratio is higher than the reference value. The term "higher" than its reference means that the value of the ratio is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or higher than its reference value. The reference value according to this particular embodiment can be the ratio between HLA-specific antibodies secreting B cells to the number of total cells secreting antibodies obtained from one or more non-transplanted subject (i.e., control subjects).

Method for Determining the Presence of Humoral Sensitization Against an HLA

In another aspect, the invention relates to an in vitro method for determining the presence of humoral sensitization against at least an HLA in a subject, hereinafter fourth method of the invention, comprising detecting the levels of antibody-secreting B cells specific for said HLA using the method of the first aspect, wherein the detection of an antibody-secreting B cell specific for said HLA is indicative of said subject having a humoral sensitization against said HLA.

The terms "in vitro", "HLA", "subject" and "antibody-secreting B cells" have been defined in relation with the first and second methods of the invention. The preferred and particular embodiments of first method of the invention regarding these terms are also included in the fifth method of the invention.

The term "humoral sensitization", as used herein, refers to the detectable presence in a subject before receiving a transplant of circulating antibodies specific for an HLA which present is in the tissue or organ candidate to be transplanted. According to the fourth method of the invention, any detectable level of said antibody-secreting B cell specific for an HLA present in the tissue or organ to be transplanted is indicative of humoral sensitization against said HLA.

In a particular embodiment, when an antibody-secreting B cell specific for said HLA is detected, the method additionally comprises a step of correlating the levels of antibody-secreting B cells specific for said HLA with a degree of humoral sensitization.

Degrees of humoral sensitization can be determined by the skilled person based on the levels of circulating antibodies specific for HLA, which is present in the tissue or organ to be transplanted. The classification of different degrees of humoral sensitization will vary depending on the techniques used for detecting said circulating antibodies against HLA from the tissue or organ to be transplanted (Lefaucheur et al., J. Am. Soc. Nephrol., 2010, 21(8): 1398-406; Claas and Doxiadis, Curr. Opin. Immunol. 2009, 21(5): 569-72; Gebel et al., Am. J. Transplant 2003; 3: 1488-1500).

The antibody specific for a HLA can be an IgG or an IgM.

In a particular embodiment, the fifth method of the invention further comprises the determination of the ratio of HLA-specific antibody-secreting B cells to the number of total cells secreting antibodies. In this particular embodiment, the detection of an increased in said ratio in a sample from the subject in relation to a reference value is indicative of said subject having a humoral sensitization against said HLA. The determination of the ratio of HLA-specific antibody-secreting B cells to the number of total cells secreting antibodies has been previously explained in relation with the first method of the invention. The term "increased" has been previously defined in relation with the second method of the invention. The reference value according to this particular embodiment has been can be the ratio between HLA-specific antibody-secreting B cells to the number of total cells secreting antibodies obtained from one or more non-transplanted subject or from one or more transplanted subjects who are known to not suffer rejection (i.e., control subjects).

Kit for Detecting Antibody-Secreting B Cells Specific for an HLA

In another aspect, the invention relates to a kit for detecting antibody-secreting B-cells specific for an HLA in a sample comprising B cells comprising an antibody specific to IgG or IgM and an HLA multimer.

As used herein, the term "kit" is used in reference to a combination of articles that facilitate the methods of the present invention. These kits provide the materials necessary for carrying out the application described herein.

The terms "antibody-secreting B cells", "HLA", "sample comprising B cells" have been previously defined in relation with the first and second methods of the invention. The preferred and particular embodiments of first method of the invention regarding these terms are also included in the second method of the invention.

The kit of the invention comprises an antibody specific to IgG or IgM. The term "antibody specific to IgG or IgM" has been previously defined in relation with the first method of the invention.

In a particular embodiment, the antibody specific to IgG or IgM is immobilized onto a solid surface, for example, onto a PVDF (polyvinylidene difluoride) plate. In a more particular embodiment, the antibody specific to IgG or IgM is immobilized onto a 96 well microplate.

The kit of the invention comprises an HLA multimer. The term "HLA multimer" has been previously defined in relation with the first method of the invention.

In a particular embodiment, the HLA multimer is a polymeric molecule to which a plurality of molecules of said HLA is attached.

In a particular embodiment, the polymeric molecule is dextran.

In a particular embodiment, a label is attached to the HLA multimer.

In another particular embodiment, the kit of the invention comprises at least two HLA multimers of different HLA. In a preferred embodiment, a different label is attached to each of the at least two HLA multimers.

In a particular embodiment, the label is a fluorochrome molecule.

The terms "polymeric molecule", "dextran", "label" and "fluorochrome molecule" have been previously defined in relation with the first method of the invention.

In a particular embodiment, the kit of the invention further comprises IL-2. The term "IL-2" has been previously defined in relation with the first method of the invention.

In a particular embodiment, the kit of the invention further comprises a TLR agonist. The term "TLR agonist" has been previously defined in relation with the first method of the invention.

In preferred embodiment, the TLR agonist is a TLR-7/8 agonist. In a more particular embodiment, the TLR-7/8 agonist is R848. The terms "TLR-7/8 agonist" and "R848" have been previously defined in relation with the first method of the invention.

In another particular embodiment, the kit of the invention further comprises an anti-CD40 antibody, preferably an agonist anti-CD40 antibody. The term "CD40" has been previously defined in relation with the first method of the invention.

In a preferred embodiment, the kit of the invention comprises IL-2 and a TLR agonist, preferably a TLR-7/8 agonist, more preferable R848.

In another preferred embodiment, the kit of the invention comprises IL-2 and an anti-CD40 antibody, preferably an agonist anti-CD40 antibody.

In another preferred embodiment, the kit of the invention comprises IL-2, a TLR agonist, preferably a TLR-7/8 agonist, more preferable R848, and an anti-CD40 antibody, preferably an agonist anti-CD40 antibody.

EXAMPLES

Example 1: HLA-B Cell Elispot Assay

1. Purpose

The enzyme-linked immunospot (Elispot) assay is a method which has been adapted for the detection of individual cells secreting antibodies against specific HLA antigens, thus allowing the detection of the frequency of circulating HLA antigen-specific memory B cells. Elispot assays employ the quantitative sandwich enzyme-linked immunosorbent assay (ELISA) technique.

Differently from assessing circulating memory/effector T cells that are abundant in the periphery, the reduced number of plasma blast circulating in peripheral blood renders this approach not feasible and reproducible enough to regularly assess antigen-specific antibody secreting B cells (ASC). Nonetheless, although memory B cells are present in the periphery, they require pre-stimulation in order to differentiate into detectable ASCs, thus an appropriate number of stimulated cells can be seeded into ELISPOTs wells to determine their HLA antigen-specific immunogenicity.

A. Definitions and Abbreviations

RPMI 1640: Roswell Park Memorial Medium 1640
PBMC: Peripherial blood mononuclear cells
Complete medium: RPMI 1640 cont. 10% FBS, 1% P/S and 2 mM L-Glutamine
FCS: Fetal bovine serum, heat inactivated for 30 minutes at 57° C.
PBS: Phosphate Buffered Saline
P/S: Penicillin/Streptomycin
BSA: Bovine serum Albumine
R848: Imidazoquinoline
DMF: Dimethylformamide
AEC: 3-Amino-9-ethylcarbozole
Blocking solution: 500 ml PBS containing 5 g BSA and sterile filtrated (0.2 um)
SEB solution: 5 ul SEB diluted in 1 ml complete medium
PBS-Tween: 500 ml PBS (unsterile=FALK solution) containing 250 ul Tween 20
PBS-Tween-BSA: 500 ml PBS (unsterile) containing 5 g BSA and filtrated and
TMB: TMB substrate
AEC Buffer: 0.1 M acetate-buffer, 352 ml 0.3 M
natriumacetate solution
Dilute up to 1000 ml, adjust at pH 5.0
Room-temperature: 19-25° C.
MLR: Mixed limphocyte reaction 3. Material and Equipment All materials in contact with cells before and during cultivation/stimulation must be sterile.

4. Procedure

All steps before and during stimulation are performed under sterile conditions in a laminar flow box. Please assure that all steps performed outside (e.g. incubation) all tubes are closed.

A. Stimulation of Memory B Cells

Either fresh or thawed PBMCs are cultured ($1.5 \times 10^6$ cells/ml, at 37° C., in 5% CO2) with culture medium (RPMI supplemented with 2 mM L-glutamine, 10% fetal calf serum, 0.1 mg/ml penicillin G and 0.1 mg/ml streptomycin) and 10 ng/ml recombinant human interleukin 2 (rhIL-2) (Mabtech) and 1 µg/ml TLR 7/8 agonist R848 (Mabtech) for 6 days in culture flasks at 37° C., 5% $CO_2$ B. Assessment of Frequency of HLA Antigen-Specific IgG Secreting B Cells (Elispot Assay)

A monoclonal antibody specific for human IgG is pre-coated onto PVDF (polyvinylidene difluoride) multiscreen Elispot plates (Millipore, Billerica, Mass., USA).

Once memory B cells have been stimulated and ASC are obtained, they can be seeded into the ELISPOT well plates and placed into a 37° C. incubator for 24 hours. During this incubation/secretion period, the immobilized antibody in the immediate vicinity of the secreting cells binds secreted antigen-specific IgG.

After washing away any cells and unbound substances, a biotinylated polyclonal antibody specific for human IgG and a fluorescent dye labeled HLA-dextramer molecule (Immudex, Denmark) is added. Following a wash, visualization of green colored spots appear at the sites of IgG localization, with each individual spot representing an individual HLA antigen-specific IgG secreting cell. Blue spots represent polyclonal IgG, giving a positive control.

The detailed protocol is as follows.

4.1 Coating

1. Dilute the coating anti IgG mAbs to 15 µg in 10 ml sterile PBS PH 7.4.
2. Remove the Elispot plate (type S5EJ104107) from the package and pre-wet with 50 µl 70% ethanol per well for maximum 2 minutes.
3. Wash plate 5 times with sterile water, 200 µl/well. Do not allow the plate to dry out during this process. If so, repeat the pre-wetting step.
4. Add 100 µl/well of the antibody solution.
5. Incubate plate overnight at 4° C.

4.2 Sample Preparation

1. Isolate PBMCs by density gradient centrifugation (Ficoll-Pâque) and prepare responder cells and stimulator cells.
2. Count cells by hematocytometer.
3. Adjust cell concentration to $1.5 \times 10^6$ in 1 ml complete medium in a 15 ml-falcon tube with a filter cap.
4. Add R848 1 µg/ml and IrhIL-2 10 ng/ml.
5. Incubate at 37° C. with 5% $CO_2$ for 72 hours.

4.3 Incubation of Cells in Plate

1. Wash plate 5 times with 200 ul/well with sterile PBS, to remove excess antibody.
2. Block microplate by adding 200 ul/well complete medium.
3. Incubate for 1 h at room temperature.
4. Wash plate with 200 ul/well PBS.
5. Wash cells from incubator tubes extensively with PBS. Make sure there is no supernatant left.
6. Count cells and adjust to adequate concentration.
7. Seed $5 \times 10^4$ cells/well per duplicates and make a 2-fold serial dilution until 2.500 cells for the total IgG determination.
8. Seed $4.5 \times 10^4$ cells/well per triplicates fir the HLA specific stimuli and make sure to have the same number of negative control wells.
9. Jacket plate in aluminium foil and incubate for 20 h at 37° C. in a $CO_2$ incubator.

4.4 Detection of Spots

Following steps are performed under unsterile conditions. Empty the plate to remove cells and wash 5×200 ul/well PBS.

A. Total IgG Spot Detection.

Prepare solution of biotin-labeled antibody 1 ug/ml PBS.

1. Add 100 ul of antibody solution to each well
2. Incubate for 2 hours at RT.

B. Antigen-Specific IgG Spot Detection.

Dilute each HLA dextramer to 100 ng/ml PBS.

1. Add 100 µl of Antigen solution to each well (including negative control wells, no IgG coated wells and no cell seeded wells).
2. Wrap the plate in aluminium foil and incubate at RT for 2-4 hours.
3. Wash the plate 5 times with PBS.
4. Add 100 µl streptavidin diluted (1:1000) to each total IgG well.
5. Add 100 µl anti-FITC green diluted 1:300 to each HLA well.
6. Incubate for 1 hour at room temperature.
7. Filtrate TMB solution (0.45 µm).
8. Wash microplate with 5×200 ul/well PBS.
9. Add 100 µl of TMB substrate solution to each total IgG well.
10. Add 100 µl of Enhancer to each HLA-specific well.

11. Incubate for 15 minutes at room temperature.
12. Dry plate overnight and count spots in an ELISPOT Bioreader.

C. Data Interpretation

A new B cell ELISPOT assay that allows a precise enumeration of the frequency of HLA-specific antibody-producing memory B cells has been developed and refined, improving several important technical features of the assay, ultimately demonstrating its potential for its use in kidney transplant recipients to determine their anti---donor humoral sensitization state:

1. The proliferative capacity of circulating B cells in antibody---secreting memory B cells has been significantly simplified and improved, strictly preserving their original antigen repertoire by using standardized supplements based on IL-2 and the TLR agonist R848 (Imidazoquinoline, Mabtech, Sweden), following a recently reported method (Jahnmatz et al., J. Immunol. Methods. 2013, 391(1-2): 50-59).
2. The detection capacity of antibody-producing memory B cells (ASC) against broad HLA-specific antigens has been significantly increased with high sensitivity and reproducibility by multimerizing single HLA proteins. In this regard, using a biotinylated polyclonal antibody specific for human IgG and a fluorescent dye-labeled (Fluorescent dye Enhancer. AID Diagnostika, Germany) HLA-dextramer molecules (Fitc labeled HLA Dextramer. Immudex, Denmark), allows clear anti-HLA IgG-spot detection and visualization using an ELISPOT reader, thus enumerating HLA-specific ASC.

Total IgG wells are used as a positive control for each subject at each time point; if a sample generates low total IgG responses, the sample has to be retested.

Memory B cells are defined as the number of ASC in the wells with stimulated cells after the subtraction of spots detected in the stimulated negative control wells (medium alone).

HLA antigen-specific memory B cell ASC is adjusted to total IgG memory B cell ASC per stimulation, allowing relative ratio calculation.

Example 2: Impact of Assessing Donor Specific Antibody-Secreting Memory B Cells (ASC) Using the B-Cell Elispot Assay in Kidney Transplant Patients The presence of donor HLA-specific ASC in different clinical conditions in kidney transplant recipients has been assessed.

Figure 2:
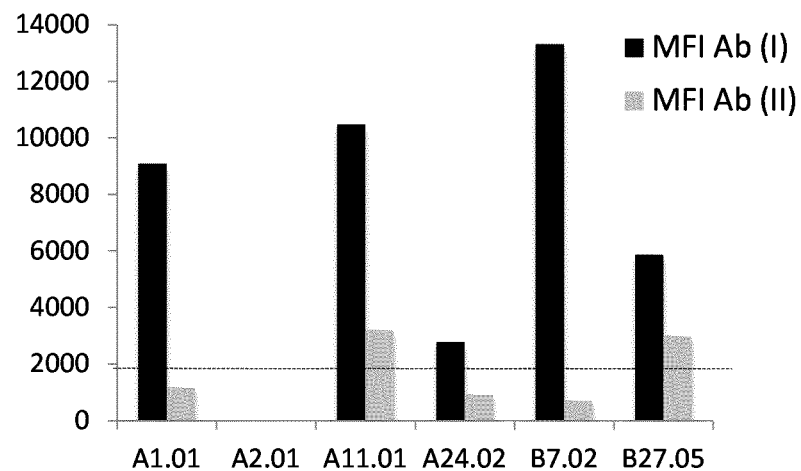
FIG. 2. A representative graphic of a hypersensitized kidney transplant patient on the waiting list showing multiple anti-HLA antibodies (with different mean fluorescent intensity, MFI) by Luminex (A01:01, A11:01, A24:02, B07:02, B27:05) at 2 different time points (MFI Ab I, MFI Ab II) (a). Each detected anti-HLA antibodies at any time point was translated in the presence of HLA-Ag-specific ASC frequencies [(b), results expressed in donor HLA-specific IgG spots (d-s IgG-ASC) and (c) as the ratio of donor HLA-specific IgG-ASC/total polyclonal IgG-ASC (d-s IgGASC/PolyIgG)].
Figure 2:
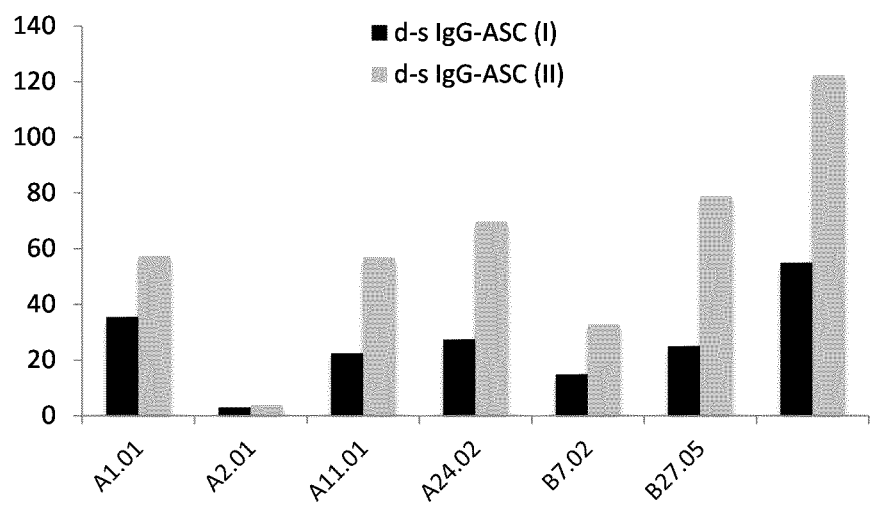
Figure 2:
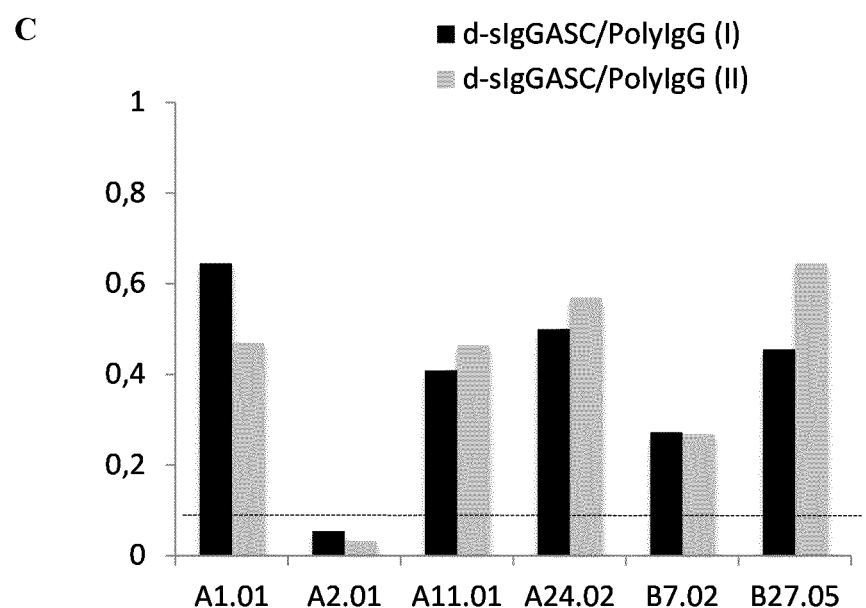
Figure 3:
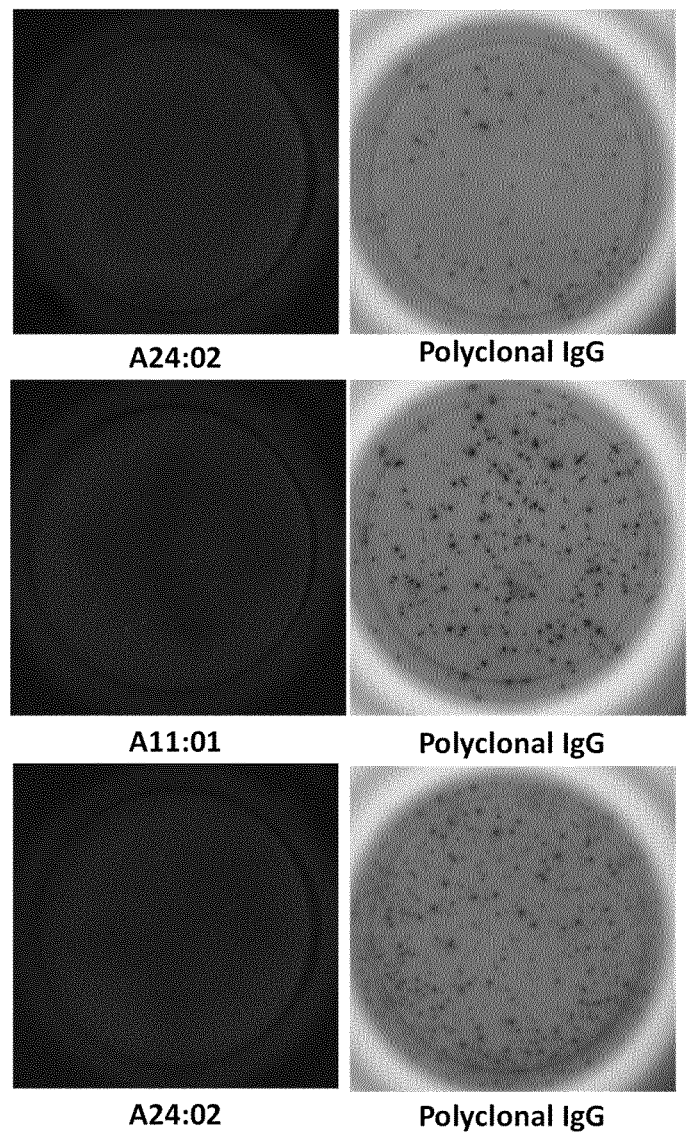
FIG. 3. Representative negative wells of a B-cell ELISPOT test against A24:02 and A11:01 in 2 patients expressing such HLA class I alleles and displaying >90% sensitization against a panel reactive antibodies (PRA). Polyclonal IgG secretion can be found in these patients as an optimal control of the ASC proliferation assay). Last panel show a representative healthy individual not showing circulating antibodies against HLA antigens assessed by LUMINEX that do not show ASC against any HLA antigens evaluated with the ELISPOT assay.
Figure 4:
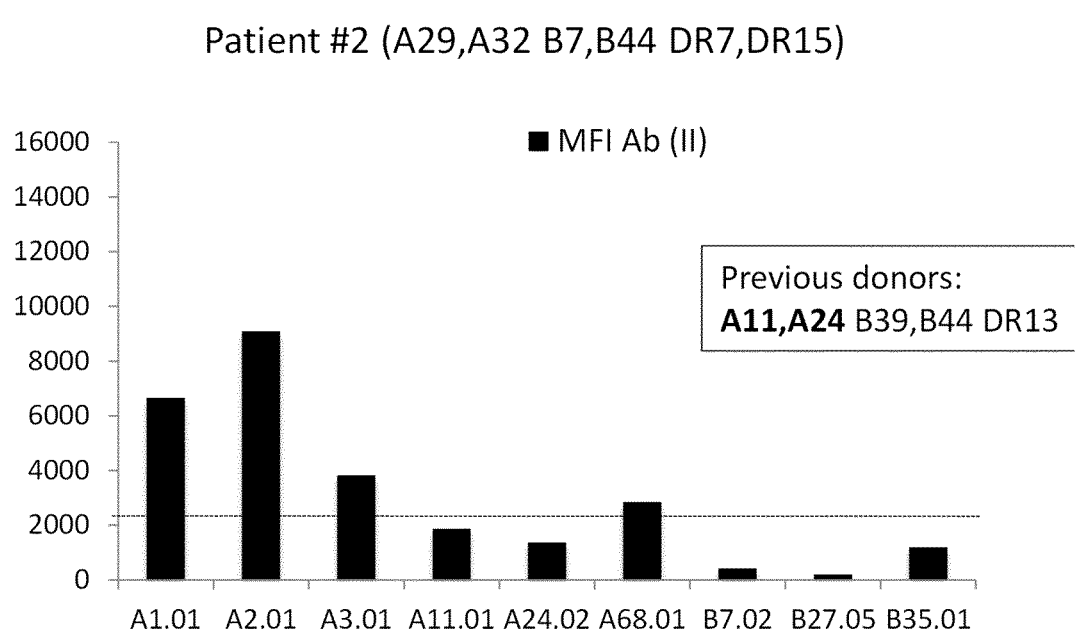
FIG. 4 shows a representative patient not currently showing circulating antibodies against the HLA antigens A11:01 and A24:02, which were expressed on the previous kidney allograft this patient had received and lost 2 years before, but did show significantly high frequencies of anti-A11:01 and anti-A24:02-specific IgG-ASC when evaluated with the B-cell Elispot assay [both donor HLA antigen-specific IgG spots (d-s IgG-ASC) and expressed by the ratio of donor HLA-specific IgG-ASC/total polyclonal IgG-ASC (d-s IgGASC/PolyIgG)].
Figure 4:
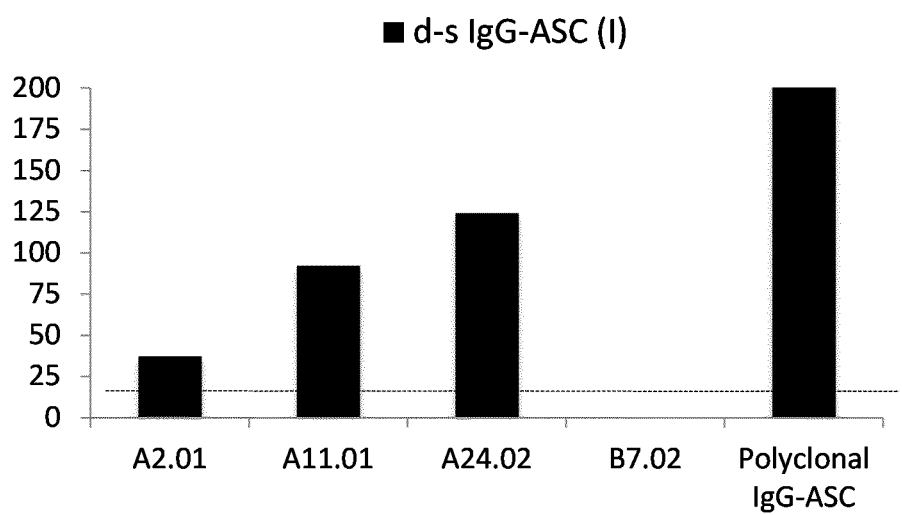
Figure 4:
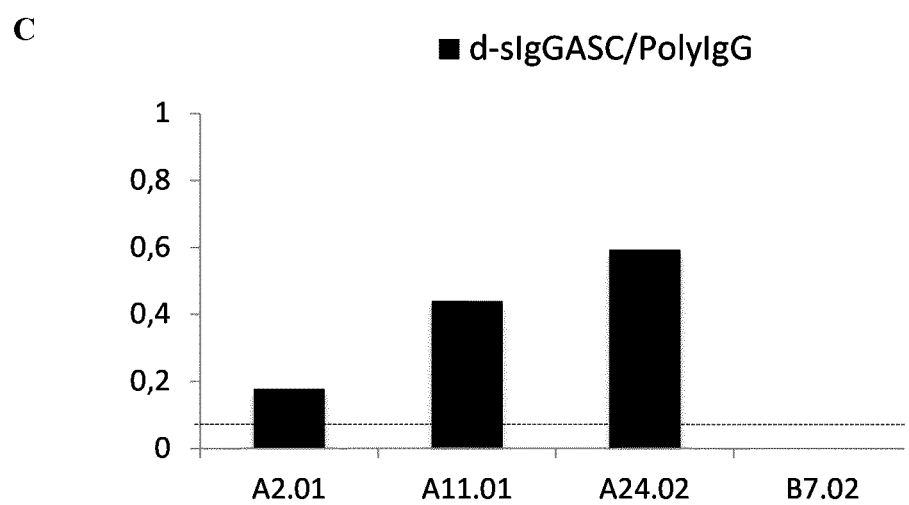
Figure 5:
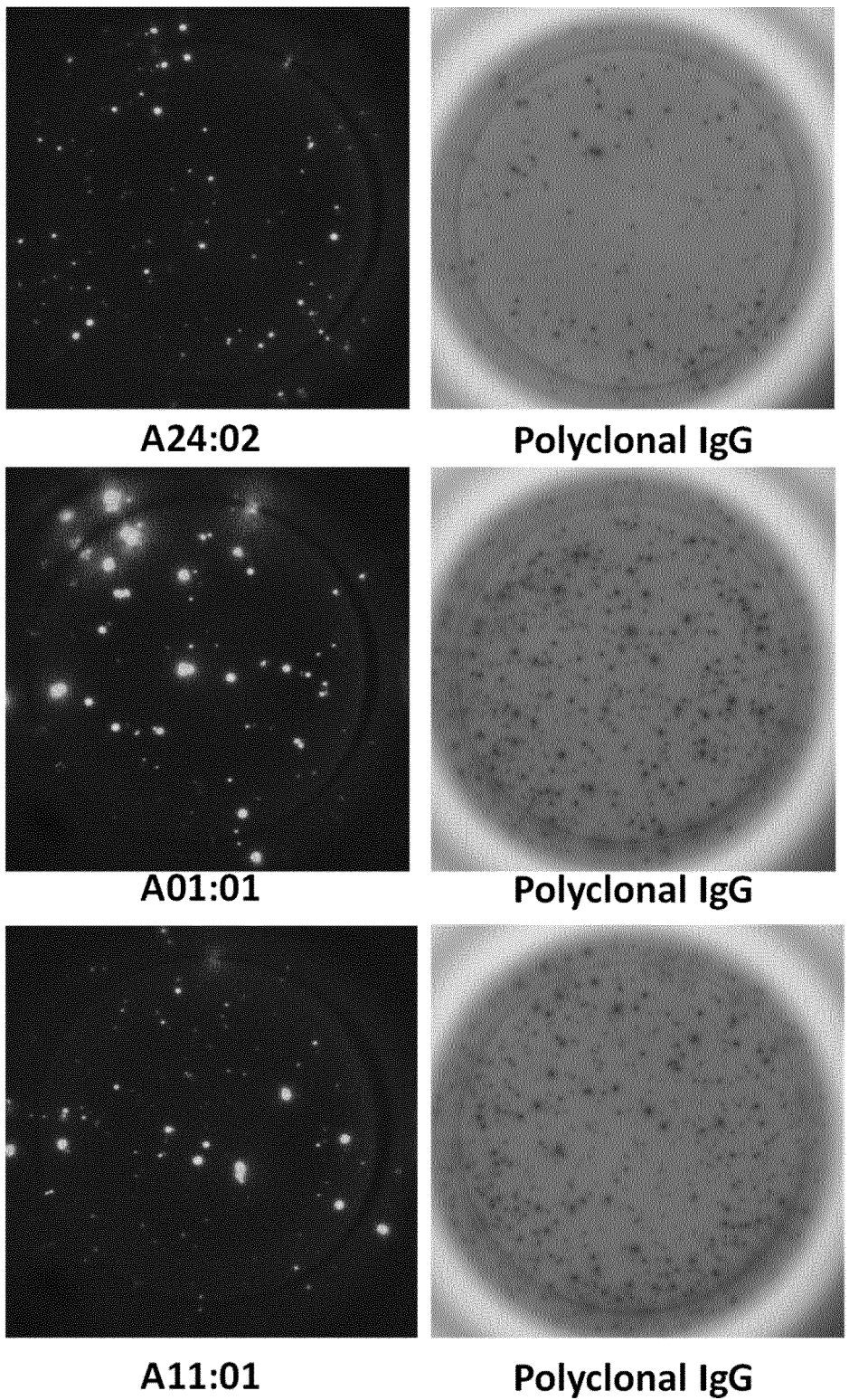
FIG. 5 shows three representative kidney transplant patients experiencing ABMR with high frequencies of donor-specific ASC against A24:02, A01:01 and A11:01 donor antigens, respectively already before and during the rejection process (The first 2 did not have circulating DSA assessed by LUMINEX assay before transplantation).
Figure 6:
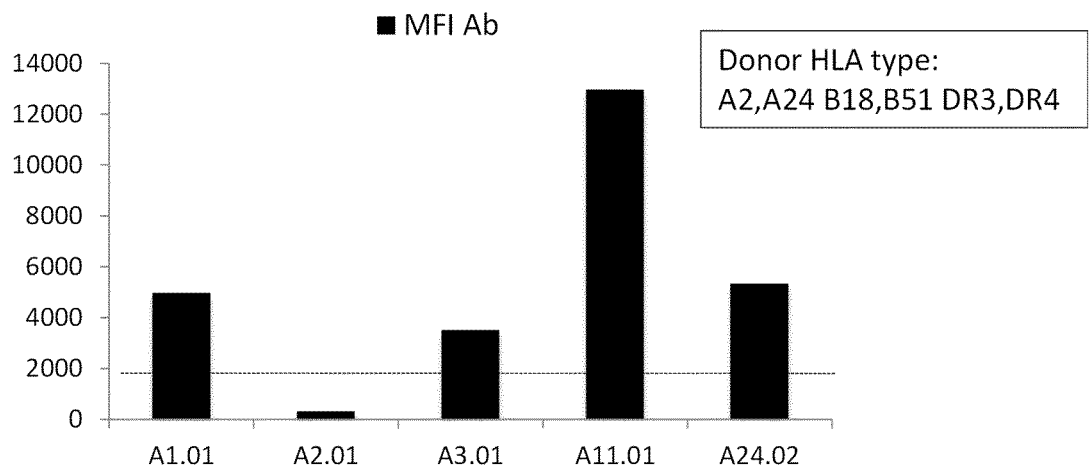
FIG. 6. shows a representative kidney transplant patient undergoing acute ABMR. While only 1 class-I donor-specific antibody (DSA) (anti-A24:02) was detected by Luminex, the B-cell Elispot assay is capable to identify high frequency of such donor-specific IgG-ASC (anti-A24:02) but also another donor-specific IgG-ASC (anti-A02:01) that was not detected using the Luminex approach (both donor HLA antigen-specific IgG spots (d-s IgG-ASC) and expressed by the ratio of donor HLA-specific IgG-ASC/total polyclonal IgG-ASC (d-s IgGASC/PolyIgG) against A24:02 and A02:01 are shown).
Figure 6:
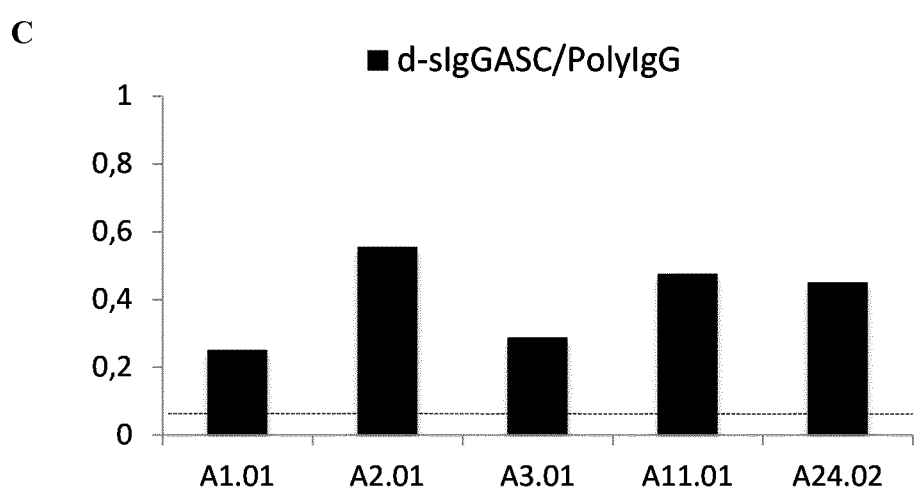
Figure 7:
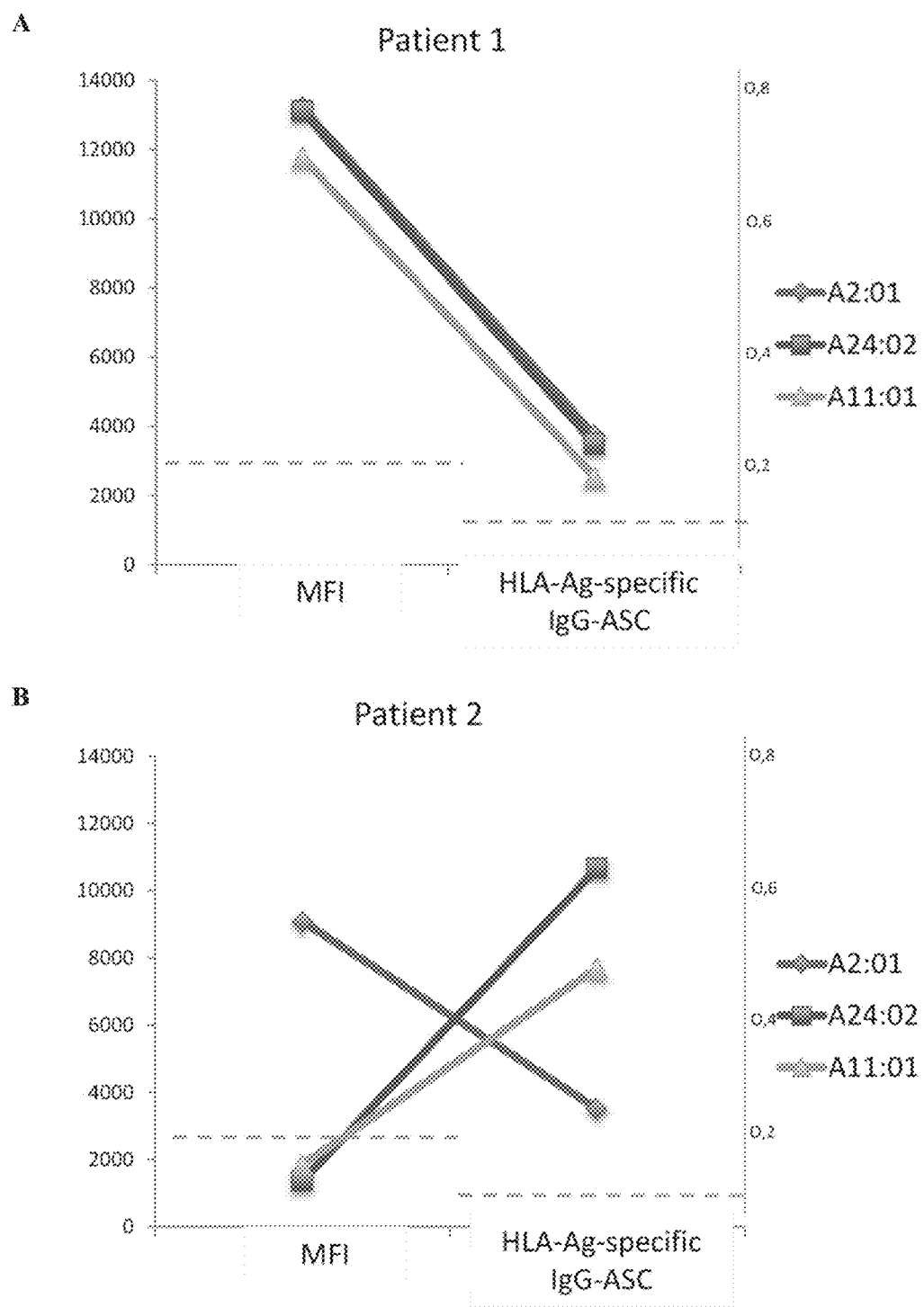
FIG. 7. Frequencies of donor-specific ASC do not always significantly correlate with the Mean fluorescence Intensity (MFI) of the detected antigen-specific antibody (HLA-Ag-specific IgG-ASC) assessed by Luminex. As shown, while patient 1 (7A) displays a highly positive correlation between MFI of each single antigen antibody and the frequency of each antigen-specific ASC, patient 2 (7B) does not show such correlation at all. Moreover, while all single antigens would have been considered as positive in patient one (MFI>2000), in patient 2 only 1 out of the 3 tested antigens would have been considered as positive despite showing high detectable frequencies of ASC against these HLA antigens FIG. 8. (A) The frequency of HLA-specific IgG-ASC was represented by the ratio between the number of HLA-specific spots over the total polyclonal IgG spots obtained in each individual. Since every patient has a determinate number of clonable memory B cells yielding to a different number of IgG-ASC after polyclonal activation, the ratio between HLA-specific IgG spots over the total polyclonal IgG spots for each patient, seems to be a reliable approach to better characterize the proportion or enhancement of a given HLA-specific IgG-ASC clone within the global IgG-ASC population. This approach method allows for qualitative and quantitative easy comparisons between samples and patients. (B) Illustrative figure of two highly HLA-sensitized Kidney Transplant patients showing the total number of polyclonal IgG spots, the number of HLA-specific IgG spots, the ratio between each HLA-specific IgG-ASC/polyclonal IgG-ASC and the MFI values of each HLA-specific circulating antibody.

1. Highly sensitized individuals against multiple HLA-specific antigens by means of circulating HLA-specific antibodies in peripheral blood assessed by LUMINEX do also show high frequency of HLA-specific ASC evaluated by the ELISPOT assay (FIGS. 1 and 2).
2. No detection of ASC against own HLA antigens after the B-cell proliferation and differentiation process and despite being highly sensitized (FIG. 3). Again, polyclonal IgG secretion can be found in these patients as a correct control of the ASC proliferation assay.
3. Some patients on the waiting list for a subsequent kidney allograft and not showing circulating HLA-specific antibodies against HLA-mismatch antigens of the previous graft do display high frequency of HLA-specific ASC assessed by the ELISPOT assay (FIG. 4). FIG. 4 shows a representative patient not showing circulating antibodies against the HLA antigens A11:01 and A24:02, which were expressed on the previous kidney allograft this patient had received and lost 2 years before, but did show significantly high frequencies of anti-A11:01 and anti-A24:02-specific IgG-ASC when evaluated with the B-cell ELISPOT assay (both HLA antigen-specific IgG spots and expressed by the ratio of HLA-specific IgG-ASC/total polyclonal IgG-ASC).
4. Patients with no evidence of donor-specific antibodies evaluated by LUMINEX before transplantation experiencing antibody-mediated rejection (ABMR) after transplantation do show high frequency of donor---specific ASC already before transplantation (FIGS. 5 and 6).
5. Interestingly, frequencies of donor-specific ASC do not always significantly correlate with the Mean fluorescence Intensity (MFI) of the detected antigen-specific antibody assessed by Luminex. As shown in FIG. 7 while patient 1 displays a highly positive correlation between MFI of each single antigen antibody and the frequency of each antigen-specific ASC, patient 2 does not show such correlation at all. Moreover, while all single antigens would have been considered as positive in patient one (MFI>2000), in patient 2 only 1 out of the 3 tested antigens would have been considered as positive despite showing high detectable frequencies of ASC against these HLA antigens.

Example 3: Validation of the B-Cell Elispot Assay in a Large Cohort of Kidney Transplant Patients Study Design All patients included in the study gave written informed consent to participate in the study, and the study was approved by the institutional review board at Bellvitge University Hospital.

The assessment of HLA-sp ASC frequencies using the newly developed B-cell Elispot assay was done evaluating 278 HLA-sp target antigens from 89 peripheral blood (PB) samples belonging to 66 patients and 4 healthy individuals. Out of the 89 PB samples obtained, 9 were excluded of the study because of insufficient ASC proliferation after the in vitro stimulation.

The main demographics of the study population are illustrated in table 1. As shown, the study population evaluated consisted of 26 highly immunized and 10 non-immunized patients on the waiting list for kidney transplantation were evaluated against specific HLA antigens. Also, 16 adult kidney transplant patients undergoing ABMR were assessed both at the time of rejection (n=16) and prior to transplantation (n=10). Also, 7 highly HLA-sensitized and 7 non-sensitized patients not developing ABMR were assessed prior to transplantation. Highly HLA immunized patients were defined as patients displaying higher than 50% panel reactive antibodies (PRA) and solid-phase bead assays. Conversely, non-immunized patients were identified as individuals with no current evidence or history of circulating antibodies using the same assays, and did not report any potential clinical evidence of allogeneic immunization such as previous transplants, blood transfusion or pregnancies.

Alloantibody Detection and Characterization

Screening for circulating donor-specific anti-HLA alloantibodies was done in banked serum samples and supernatants of B-cell cultures. Antibody specificities against both class I and II HLA antigens were determined using single-antigen flow beads assays (One-lambda Inc.) on a Luminex platform.

TABLE 1

Main clinical demographic characteristics

| Main clinical and demographic characteristics (patients with ABMR) | ABMR (N = 16) | No ABMR (N = 14) | |
|---|---|---|---|
| | | Sensitized (N = 7) | Non Sensitized (N = 7) |
| Gender (female, %) | 8 (50) | 4 (57) | 1 (14.3) |
| Age (years, mean ± SD) | 52.9 ± 12.3 | 49 ± 8.1 | 48.2 ± 15.3 |
| Race (caucasian, %) | 16 (100) | 6 (85.7) | 6 (85.7) |
| Type of kidney TX (deceased, %) | 3 (18.7) | 3 (42.8) | 3 (42.8) |
| Previous Transplants (mean ± SD) (range) | 1.3 ± 0.75 (0-3) | 1.3 ± 0.48(0-1) | 0(0) |
| Time on dialysis prior to TX (months) | 18.9 ± 12.6 | 19.4 ± 10 | 12.1 ± 10 |
| Induction IS (%) | | | |
| rATG/Basiliximab (%) | 12(75)/4(25) | 5(71.4)/2(28.6) | 2(28.6)/5(71.4) |
| Plasmapheresis/IVIG (%) | 2(12.5)/11(68.75) | 1(14.3)/6(85.7) | 0(0)/0(0) |
| Maintenance IS | | | |
| CNI-based (TAC/CsA) (%) | 15(93.75)/1(6.25) | 6(85.7)/1(14.3) | 7(100)/0(0) |
| Mean time of diagnosis ABMR (months) | 3.8 ± 2.7 | NAp | NAp |
| Pre-Transplant cPRA (mean % ± SD) | 53 ± 30 | 52.8(24.78) | 0(0) |
| Pre-Transplant CDC cross-match | Negative | Negative | Negative |
| Extend of ABMR injury | | NAp | NAp |
| Vascular rejection (yes/%) | 7 (43.75) | | |
| TCMR (yes/%) | 2 (12.5) | | |
| TCMR and Vascular rejection (yes/%) | 0 (0) | | |
| Allograft histology lesions by compartments (Banff scores), (mean ± SD; range) | | NAp | NAp |
| Glomerulitis (ag) | 1.75 ± 1 (0-3) | | |
| Interstitial inflammation (ai) | 1.7 ± 0.7 (0-3) | | |
| Tubulitis (at) | 1 ± 0.7 (0-2) | | |
| Peritubular capillaritis (ptc) | 1.8 ± 1 (0-3) | | |
| Endothelialitis (av) | 1 ± 1.2 (0-3) | | |
| C4d+ | 1.4 ± 0.8 (0-3) | | |

Flow-Cytometry Cross-Match (FCXM)

The flow-cytometry cross-match (FCXM) was performed for those kidney transplant recipients in whom donor cells (either splenic or peripheral lymphocytes) and recipient sera were available at the time of transplant surgery. For the FCXM, 100 ul of a $2.5 \times 10^6$ cells/ml donor cell suspension was mixed with 20 ul of appropriate test and control sera. Samples were incubated for 20 min at 4° C. then centrifuged and washed three times with cold phosphate-buffered saline. Fluorescence-labeled antibodies (3 ul anti-CD3 PerCP, 3 ul anti-CD19 phycoerythrin, and 20 ul of a working dilution of anti-human IgG F[ab]' FITC) were then added. After a 20-min dark incubation, two wash steps with phosphate-buffered saline were performed, and lymphocytes were resuspended in 500 ul phosphate-buffered saline with 0.05% sodium azide and transferred into tubes for analysis. Three-color flow cytometric analysis was performed with a FAC-SCalibur instrument (BD Biosciences, Sp). Lymphocytes were gated on the basis of their forward and side-scatter characteristics. With a scale that expressed staining intensity as a linear channel value (0 to 1024), median channel fluorescence for anti-human IgG F(ab)' FITC was quantified on CD3+ T cells and CD19+ B cells. A positive cross-match was identified when the sample median fluorescence intensity exceeded that of negative control values by 3 SD. SD were derived by performing negative control FCXM with sera from 10 AB-negative non transfused males and lymphocytes from 15 healthy donors (data not shown). A positive T cell FCXM and a positive B cell FCXM represented median channel shift values of 240 and >100, respectively.

Renal Allograft Histology

Renal allograft biopsies used to characterize antibody-mediated rejection were all performed for cause due to clinical allograft dysfunction and were evaluated following the Banff score classification.

Assessment of HLA-Specific Memory IgG-Antibody Secreting B Cells

Memory B Cell Stimulation Assay

To induce and differentiate circulating memory B cells to antibody-secreting cells (ASCs), PBMCs were cultured ($1.5 \times 10^6$ cells/ml, at 37° C., in 5% $CO_2$) for 6 days in Roswell Park Memorial Institute (RPMI) medium (supplemented with 2 mM L-glutamine), 10% fetal calf serum, 0.1 mg/ml penicillin G (Britannia Pharmaceuticals®, UK), 0.1 mg/ml streptomycin (Sigma-Aldrich®, 10 ng/ml recombinant human interleukin 2 (rhIL-2) (Mabtech®, Sweden), and 1 µg/ml toll-like receptors 7/8 agonist R848 (Mabtech®, Sweden). After such stimulation, memory B cells proliferate and differentiate into ASCs. A significant number of memory B cells proliferated and differentiated into ASCs. After thorough washing, the cells were used in IgG B-cell ELISPOT assays.

HLA-Specific IgG B-Cell ELISPOT Assay

For the detection of frequencies of HLA-specific IgG-antibody secreting cells (HLA-specific IgG-ASC), the newly developed HLA B-cell ELISPOT system was used, with slight modifications. Briefly, $4.5 \times 10^5$ cells from the previously described memory B cell stimulation assay were seeded in 10011 well triplicates on an IgG pre-coated PVDF (polyvinylidene difluoride) multiscreen Elispot plates (Millipore®, Billerica, Mass., USA) and placed into a 37° C. incubator for 24 hours. 100 µl of complete medium was added in separate wells and used as negative controls. After washing away any cells and unbound substances, a fluorescent dye labeled class I and II HLA dextramers (Immudex®, Denmark) was added to each well. Following a wash, and adding 100 µl diluted anti-FITC green dilution, visualization of green colored spots appear at the sites of IgG localization, with each individual spot representing an individual HLA-specific IgG-ASC. For total polyclonal IgG-ASC detection, a previously described protocol was followed (Jahnmatz et al., 2013, Methods 391:50-9). Briefly, $4.5 \times 10^4$ cells were seeded per anti-IgG coated well and after a 24 h 37° C. incubation a streptavidine-alkaline phosphatase (AP) and (BCIP) substrate detection system yielded blue spots corresponding to polyclonal IgG-ASC. Spot-forming cells were subsequently enumerated in semiautomatic mode using AID® ELISPOT Reader HR, $4^{th}$ generation.

Total polyclonal IgG wells were used as a positive control for each subject per stimulation; if a sample generated low total polyclonal IgG responses (<20 IgG polyclonal spots/$4.5 \times 10^4$ ASC), the sample was not considered for the study.

Figure 8:
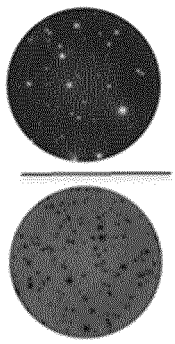

Unspecific spots detected in the negative control wells (medium alone) if any, were subtracted from the resulting HLA-specific spot count. HLA-specific IgG-spot forming-cell frequencies within the total polyclonal IgG-ASC were represented as a ratio (HLA-sp spots number/IgG polyclonal spots number) allowing a better characterization of the proportion or enhancement of HLA-sp IgG-ASC clones within the complete IgG-ASC population, as shown in FIGS. 8A and 8B.

Statistical Analysis

Figure 9:
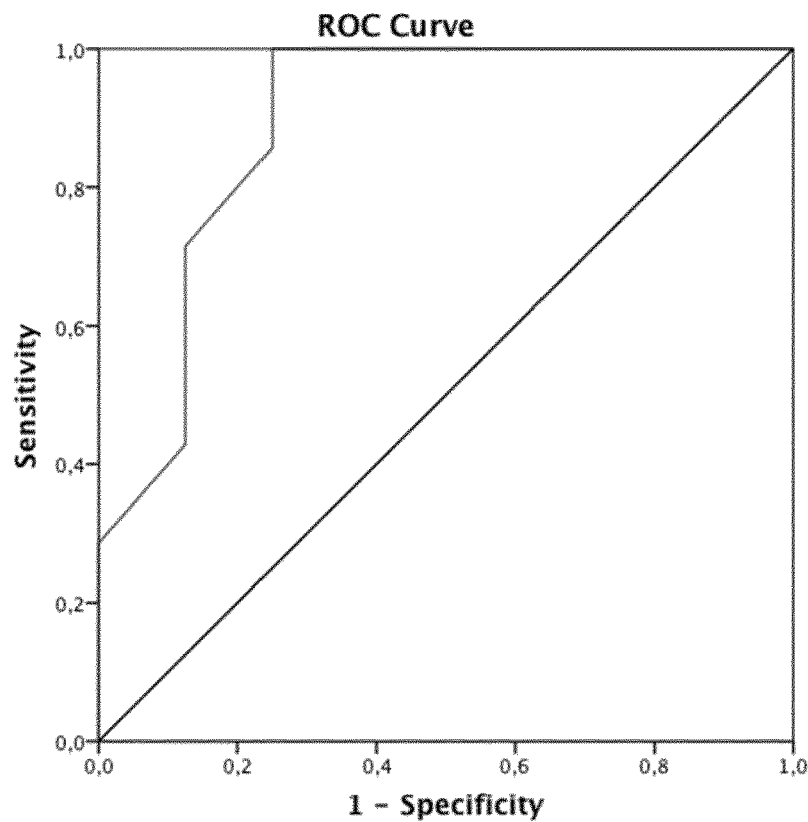
FIG. 9. A sensitivity/specificity receiver operating characteristic analysis was performed to evaluate the most precise cut-off anti-donor HLA B-cell Elispot ratio (donor-specific IgG-ASC/polyclonal IgG-ASC) assessed at the time of acute ABMR predicting the advent of acute vascular lesions following the Banff score classification. As shown, 0.35 was the most sensitive (85.7%) and specific (75%) donor HLA-sp B-cell Elispot ratio predicting the presence of endarteritis (AUC=0.893; p=0.011; CI95% (0.721-1).

All data are presented as mean±standard deviation (SD). Groups were compared using the $\chi^2$ test for categorical variables, the one-way analysis of variance (ANOVA) or t-test for normally distributed data, and the nonparametric Kruskal-Wallis or Mann-Whitney U test for non-normally distributed variables. Bivariate correlation analyses were done using Pearson or spearman tests for non-parametric variables. A sensitivity/specificity receiver operating characteristic analysis was performed to evaluate the most precise cut-off of the anti-donor HLA B-cell Elispot ratio (donor-specific IgG-ASC/polyclonal IgG-ASC) assessed at the time of acute ABMR predicting the advent of acute vascular lesions following the Banff score classification (FIG. 9). The 2-tailed statistical significance level was p<0.05.

Results

1. The HLA-Specific B-Cell Elispot is Highly Specific to Detect Frequencies of Both Class I and II HLA-Specific IgG-Antibody Secreting Cells (ASC)

Figure 10:
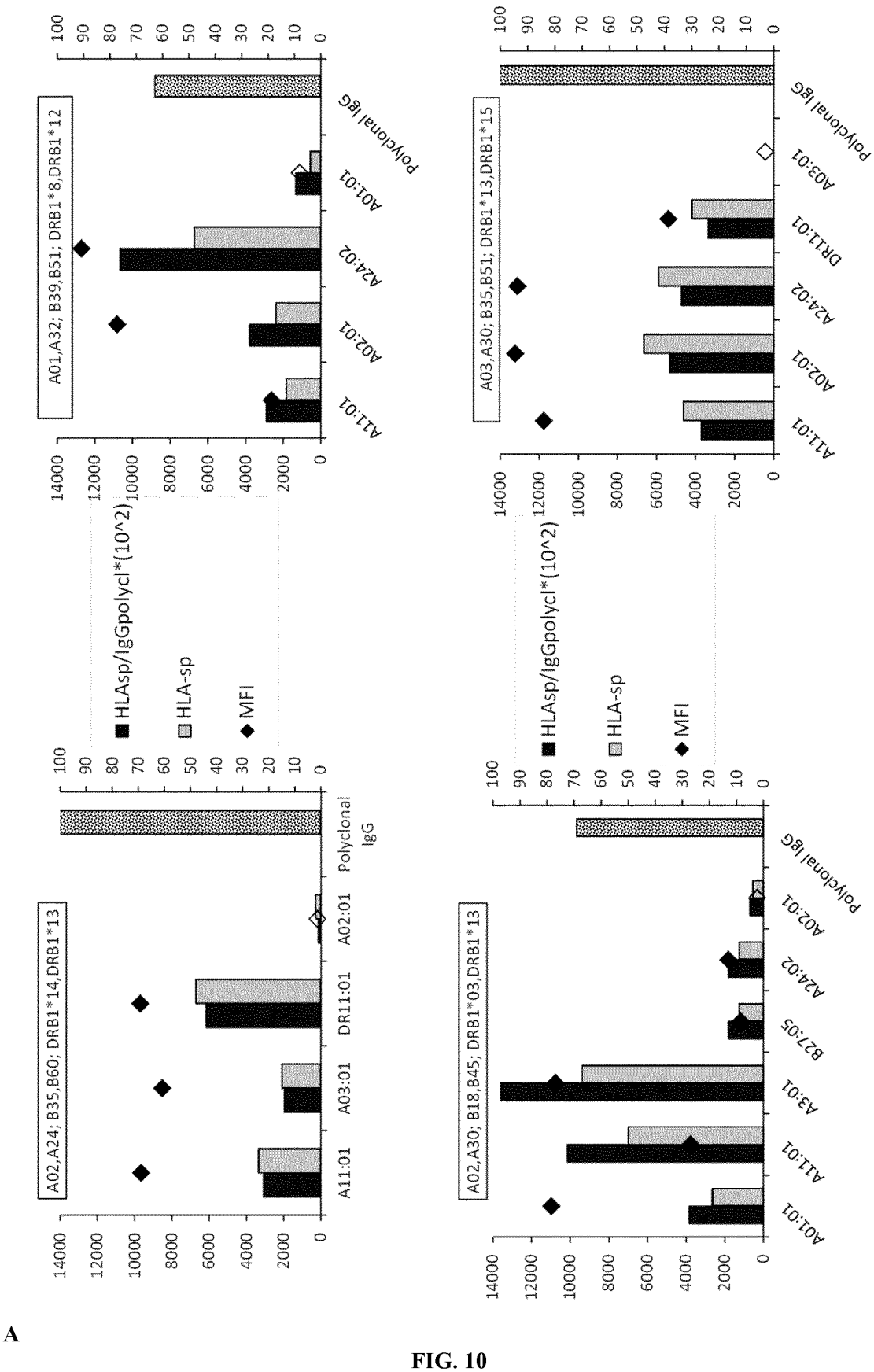
FIG. 10. Assessment of HLA-specific IgG-ASC frequencies among highly HLA immunized and non-immunized patients. (A) Representative HLA B-cell Elispot plots of 4 highly HLA immunized patients. As shown, a wide range of HLA-sp IgG-ASC frequencies as well as the ratio of HLA-sp IgG-ASC responses over total polyclonal IgG-ASC against the targeted class I and II HLA antigens is observed. Different polyclonal IgG-ASC frequencies may be seen for each patient. No HLA-sp IgG-ASC frequencies were observed against own HLA-typed antigens in any individual. (B) Representative HLA B-cell Elispot plots of 2 non-HLA immunized patients and 2 healthy individuals. As shown, no evidence of HLA-sp IgG-ASC responses in peripheral blood can be detected despite robust polyclonal IgG-ASC frequencies among all individuals. Grey diamonds represent the MFI antibody level (left Y axis); empty diamonds represent antibodies that would have been considered as negative following the in-house threshold for a negative or positive detection in the Luminex platform (2000 MFI). Columns represent the number of HLA-sp IgG spots (light grey), the ratio of HLA-sp ASC/polyclonal IgG-ASC (dark grey) or total polyclonal IgG spots (pointed column) (right Y axis).
Figure 10:
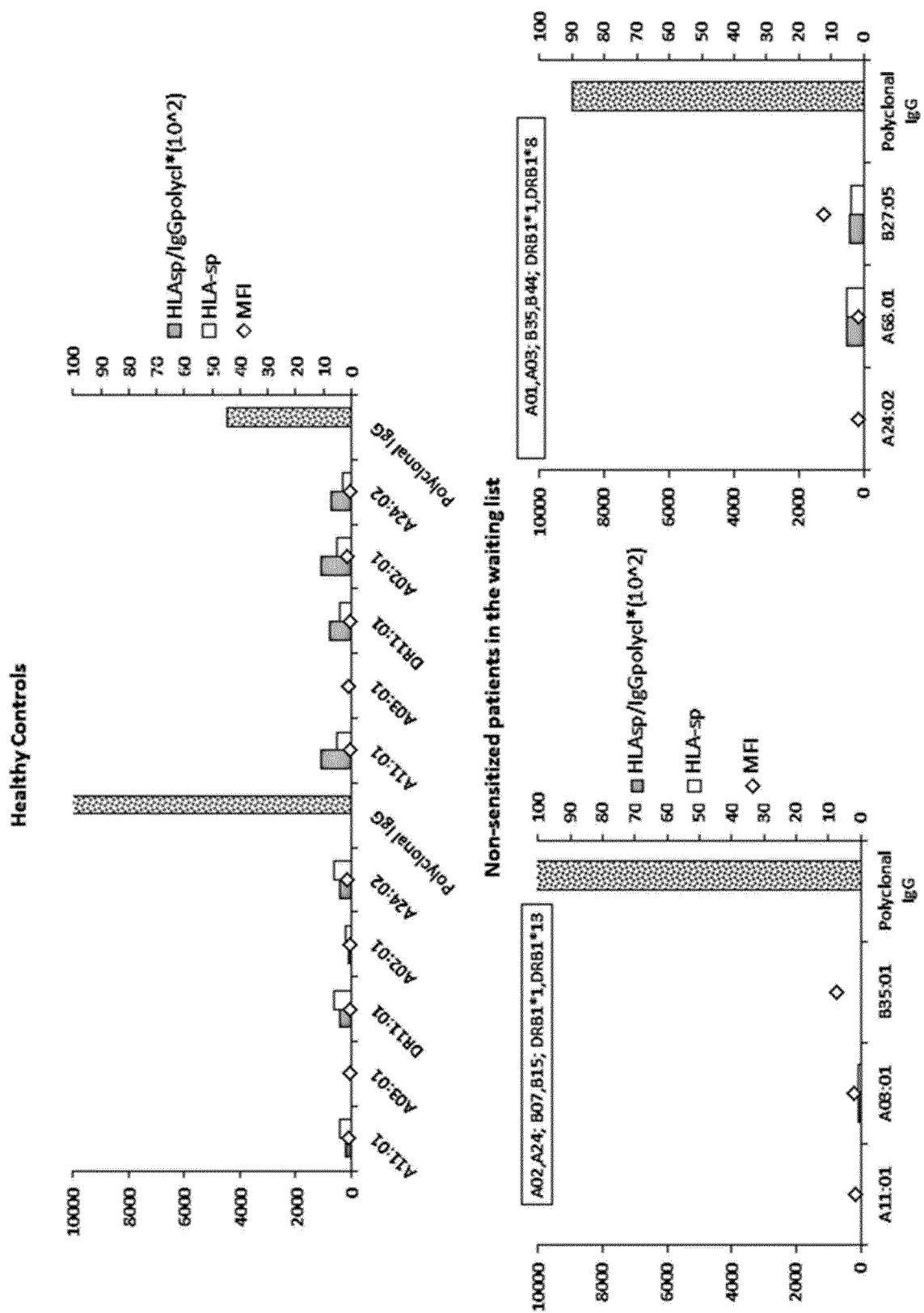

Highly HLA-immunized patients were evaluated with the newly developed HLA B-cell Elispot assay to determine the frequency of HLA-sp IgG-ASC against different specific class I and II well-characterized HLA antigens. With this technique, the presence of memory B cells specific to HLA antigens is analyzed, since the original source of the ASC is the memory B cells. As shown in FIG. 10A, a wide range of HLA-sp IgG-ASC frequencies as well as the ratio of HLA-sp IgG-ASC responses over total polyclonal IgG-ASC against the targeted class I and II HLA antigens was observed in all sensitized patients. No HLA-sp IgG-ASC frequencies were observed against own HLA-typed antigens in any individual.

The same evaluation among healthy individuals and non HLA-immunized patients, revealed no evidence of HLA-sp IgG-ASC responses in peripheral blood (FIG. 10B). All screened patients displayed a broad range of polyclonal IgG-ASC frequencies, demonstrating the viability of all tested ASC.

The HLA-sp IgG B-cell Elispots were confirmed as HLA-specific antibodies by its detection in the corresponding supernatants using the Luminex platform.

Figure 11:
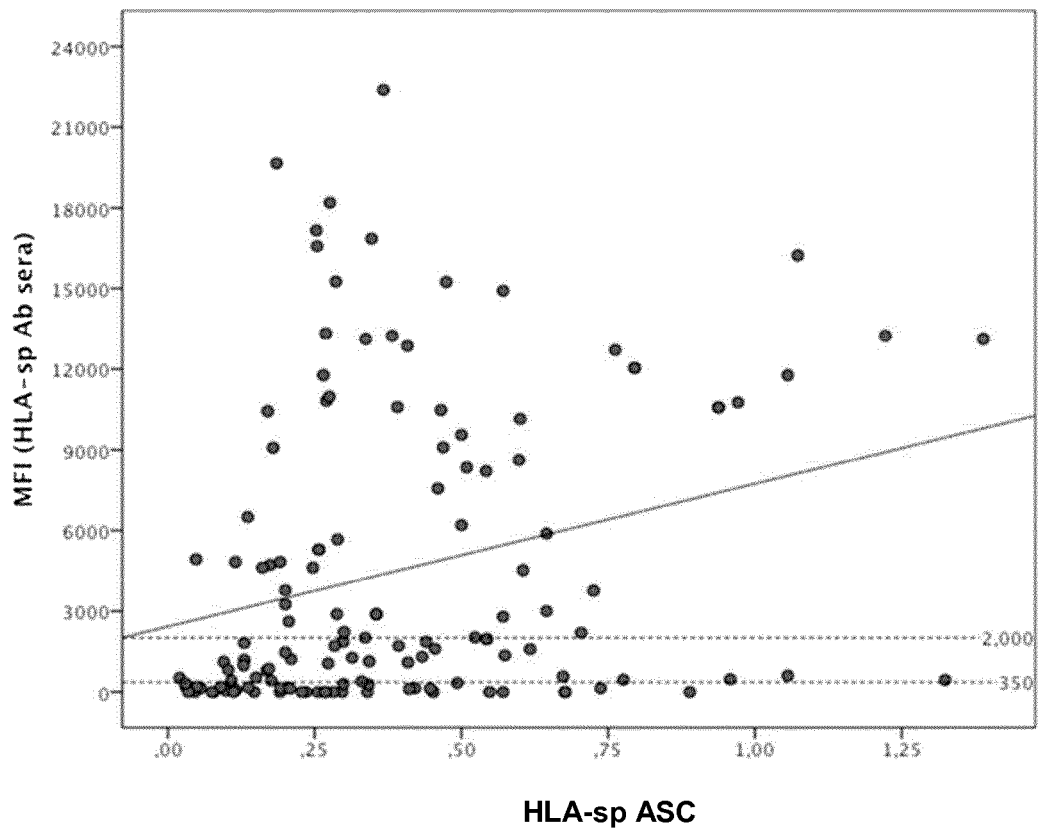
FIG. 11. Correlation between the Mean Fluorescence Intensity (MFI) antibody level in sera and HLA-specific IgG-ASC frequencies. (A) A weak positive correlation was observed between the ratio of HLA-sp IgG-ASC/polyclonal IgG-ASC frequencies and the MFI antibody level (r=0.31, p=0.001). (B) No correlation was observed between total polyclonal IgG-ASC and the MFI (p=NS). The dots above or below the 2000 MFI cut-off, represent values that would have been considered as positive or negative, respectively, following the in-house threshold for a positive or negative detection in the Luminex platform (2000 MFI).
Figure 11:
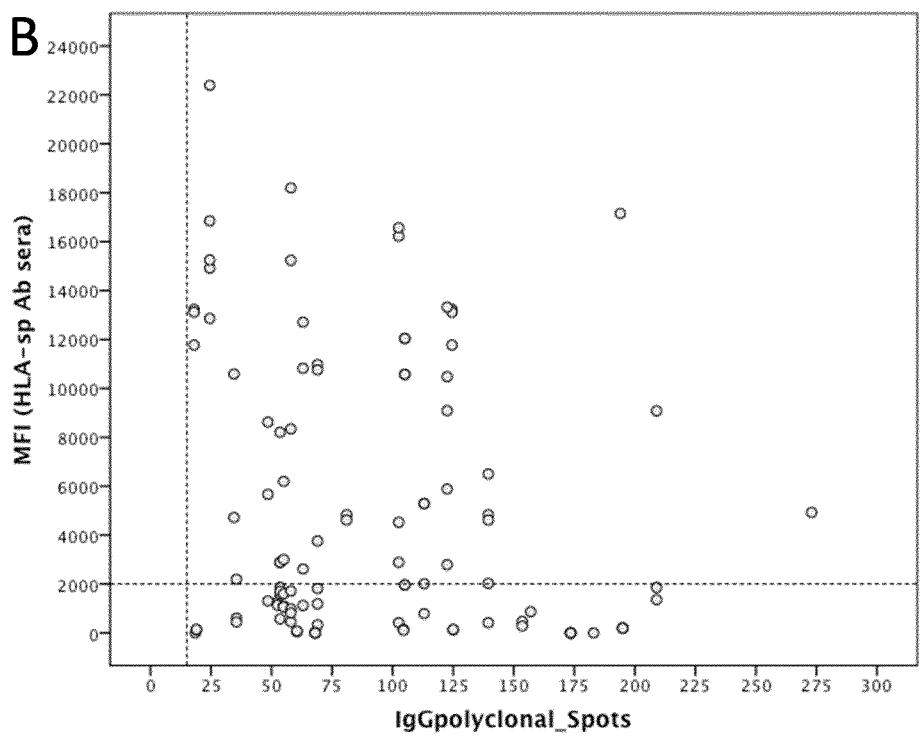

2. High Frequencies of Circulating HLA-Specific IgG-Antibody Secreting Cells May be Detected Regardless the Presence of Circulating HLA-Specific Antibodies Next, it was aimed to evaluate whether there was any association between the frequency of the HLA-sp ASC and the strength of circulating HLA-sp Ab (MFI) in highly HLA-sensitized patients. As shown in FIG. 11, a weak but significant positive correlation between HLA-sp ASC frequencies and HLA-sp antibody MFIs in the serum was observed (r=0.31, p<0.001).

Of note, circulating alloreactive HLA-sp ASC responses could also be detected despite low MFI levels (MFI<1500) and even in absence of circulating HLA-sp antibodies in some evaluated cases, 42/136 (30.8%). As displayed in table 2, main immunologic variables associated to HLA-sp ASC responses within HLA seronegative patients (HLA-sp ASC+/HLA-sp Ab−), revealed clear signs of previous HLA-sp sensitization either by detection of such alloantibodies at previous time points or because of former exposure to such HLA-mismatched alloantigens in preceding failed kidney allografts, similarly to HLA-sp seropositive patients (HLA-sp ASC+/HLA-sp Ab+). However, the strength of both HLA-sp ASC frequencies and HLA-sp antibody MFIs were significantly higher in patients with detectable HLA-sp antibodies as compared to seronegative individuals.

TABLE 2

Main epidemiologic and immunologic variables associated to HLA-sp memory B cell responses within HLA IgG-seronegative patients

| Main immunological characteristics | HLA-sp ASC+ and HLA-sp Ab+ (N = 67/136) | HLA-sp ASC+ and HLA-sp Ab− (N = 42/136) | P-value |
| --- | --- | --- | --- |
| HLA-sp Ab MFI (mean ± SD) | 8143.4 ± 5341.4 | 440.5 ± 453 | <0.001 |
| HLA-sp ASC (mean ± SD) | 0.38 ± 0.2 | 0.22 ± 0.2 | 0.007 |
| Total polyclonal IgG-ASC (mean ± SD) | 76.92 ± 40 | 88.4 ± 63.2 | NS |
| HLA-mismatch Ag harbored in previous kidney allografts (N/%) | 52 (81%) | 30 (71%) | NS |
| Prior detection of HLA-sp Ab (Yes, %) | 50 (78%) | 29 (69%) | NS |

Abbreviations:
POS, positive;
NEG, negative;
HLA, human leucocyte antigens;
Ab, antibodies,
DSA, donor-specific antibodies,
MFI, mean fluorescence intensity;
HLA-sp, HLA-specific;
IgG-ASC, IgG-antibody secreting cells;
Polycl, polyclonal;
BCE, B-cell Elispot,
SD, standard deviation.

Figure 12:
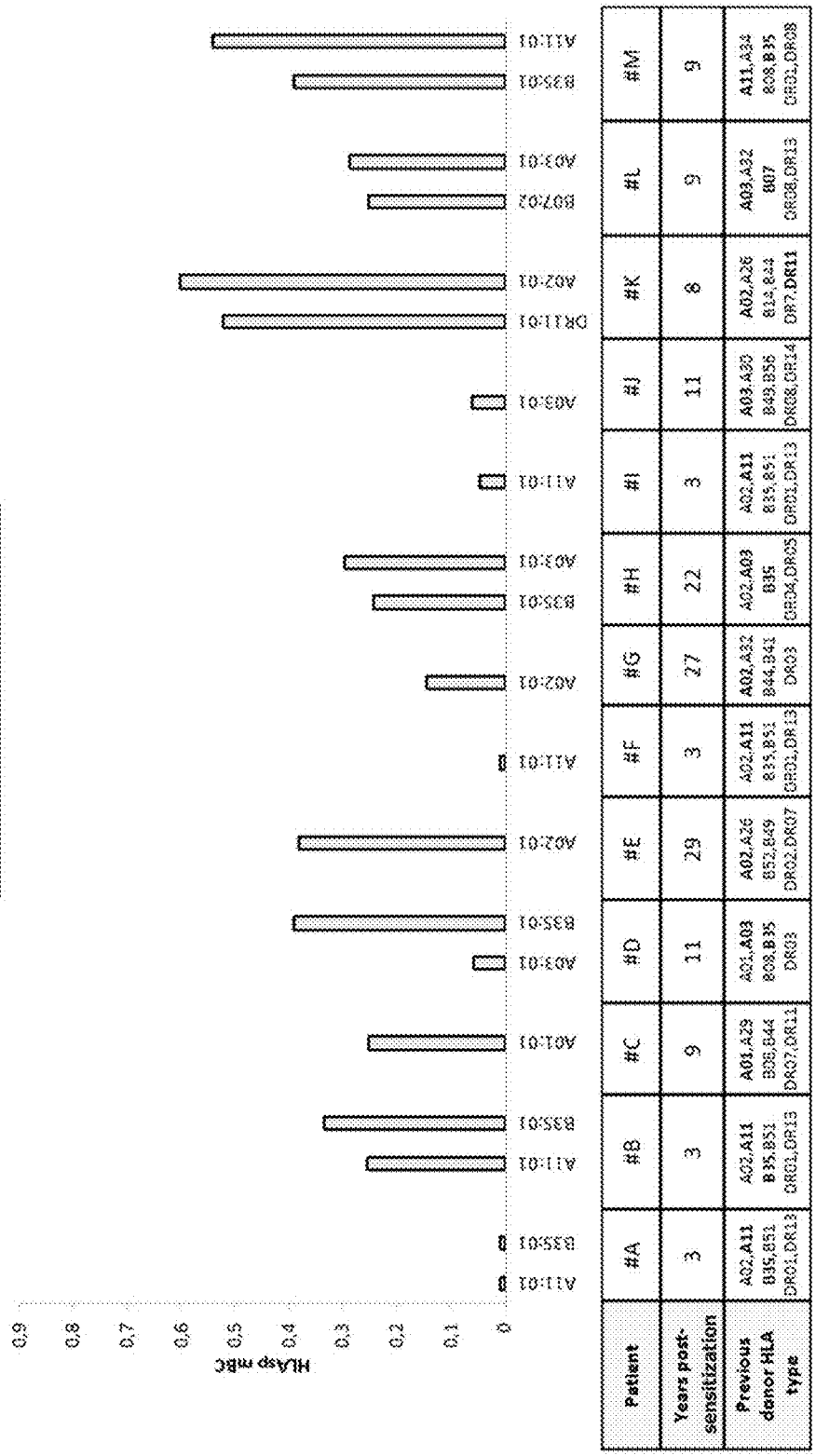
FIG. 12. HLA-sp antibody secreting cells (ASC) frequencies may be detected in sensitized patients against HLA antigens harbored in previous allografts. HLA-sp ASC frequencies were detected against HLA antigens expressed in previous kidney allografts in various patients. HLA-sp ASC responses were found in patients that had been transplanted 3 years before (patients #B, #1) and also in 3 patients that received the kidney allograft more than 20 years before (patients #E 29 years, #G 27 years and #H 22 years ago). Nonetheless, in other patients (patients #A and #F), no frequencies could be detected in peripheral blood.

3. HLA-Specific ASC May be Detected in Sensitized Patients Against HLA Antigens Harbored in Previous Allografts Previously transplanted patients were evaluated for HLA-sp ASC responses against HLA-sp antigens harbored in previous allografts. As observed in FIG. 12, HLA-sp ASC frequencies were detected against certain HLA antigens expressed in previous kidney allografts, even in patients transplanted more than 20 years before (patients #E, #G, #H), whereas in some others, HLA-sp ASC frequencies were not observed (patient #A). Time of sensitization or duration of the functioning graft did not correlate with the HLA-sp ASC frequency.

Figure 13:
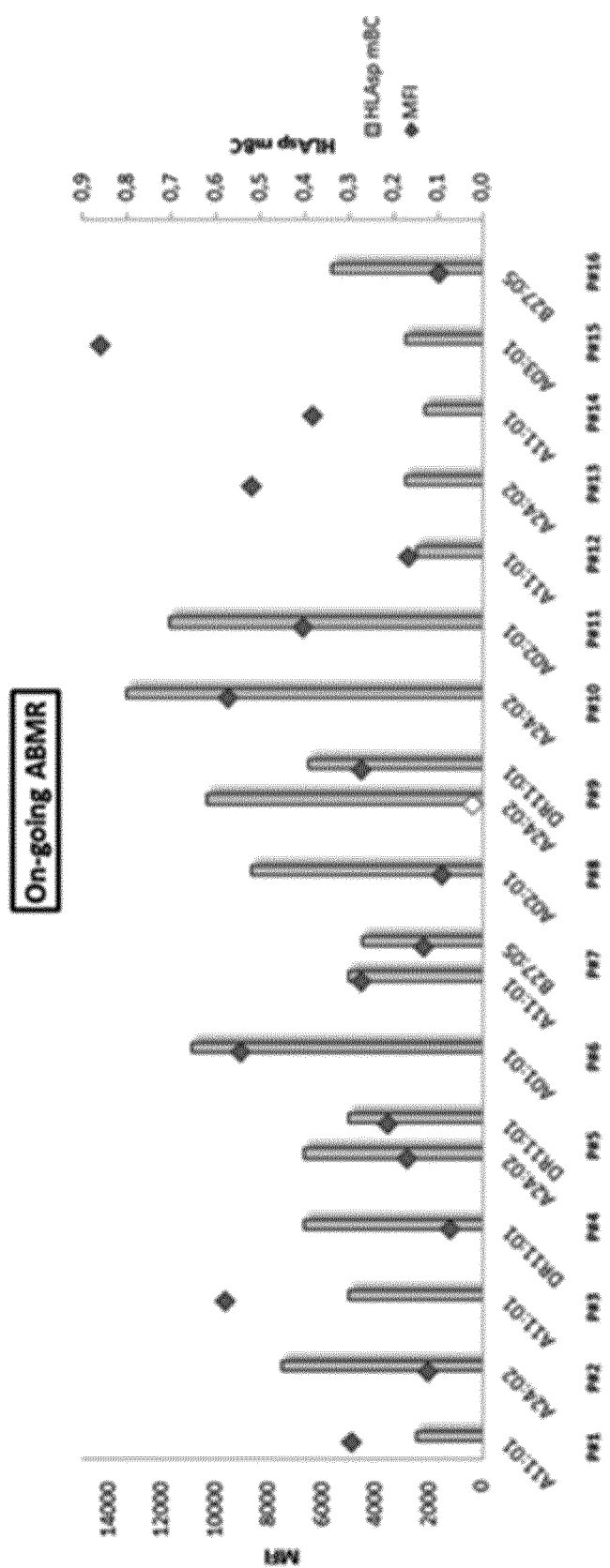
FIG. 13. HLA-specific IgG-ASC frequencies of kidney transplant patients at time of ABMR and prior to receive the kidney allograft. (A) Ratio of donor-specific HLA-sp IgG-ASC/polyclonal IgG-ASC frequencies in kidney transplant patients at the time of ABMR. All patients showed a broad range of d-s alloreactive ASC frequencies in peripheral blood. Interestingly, in one patient (p#9), while only 1 circulating DSA (DR11:01) was detected, the B-cell Elispot revealed the presence of an additional d-s ASC clone that had actually been previously observed in the circulation (DR11:01 and also A24:02). (B) Ratio of pre-transplant donor-specific HLA-sp IgG-ASC/polyclonal IgG-ASC frequencies in 10/16 kidney transplant patients that developed acute ABMR after transplantation. As illustrated, an important proportion of the evaluated patients already had d-s ASC frequencies circulating, most of them fitting with clear previous sensitization process. Conversely, the only patient without d-s ASC response (patient #4) did not have previous sensitization events thus, suggesting a de novo activation of the anti-donor humoral immunity. Black diamonds represent the MFI antibody level (left Y axis), empty diamonds represent HLA-specific ASC, i.e. antibodies that would have been considered as negative following the in-house threshold for a negative or positive detection in the Luminex platform. Columns represent the ratio of HLA-sp ASC/polyclonal IgG-ASC (right Y axis).
Figure 13:
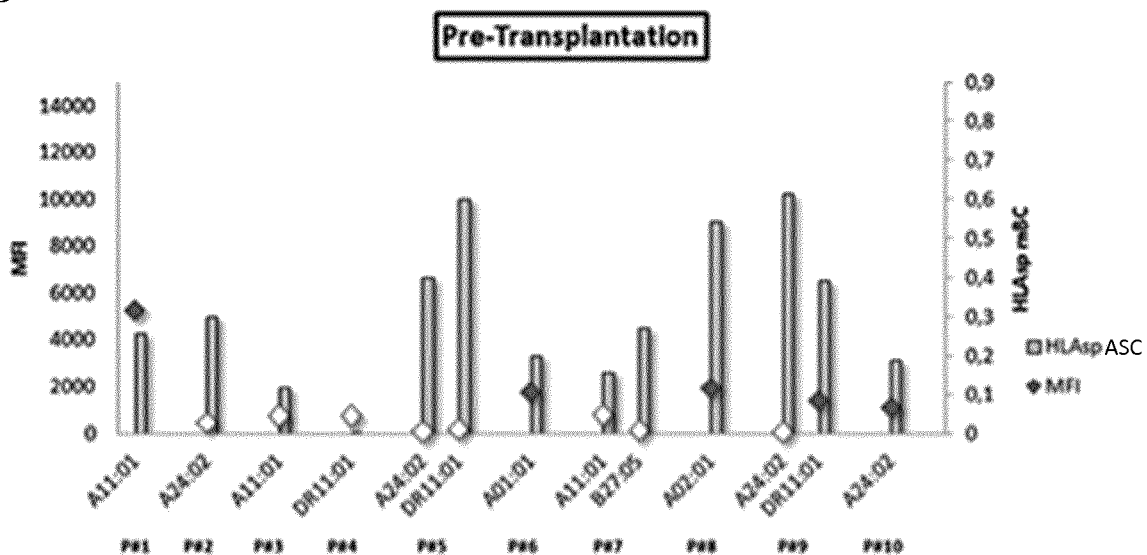

4. Patients Undergoing Antibody-Mediated Rejection (ABMR) Display High Frequencies of Donor HLA-Specific IgG-Antibody Secreting Cells in Peripheral Blood Subsequently, circulating donor HLA-specific (d-s) ASC of kidney transplant recipients were analyzed both at the time of acute ABMR (n=16) and prior to transplantation (n=10). As shown in FIG. 13a and detailed in table 3, during ABMR, all evaluated patients showed a broad range of detectable alloreactive d-s HLA-ASC frequencies fitting with the presence of the corresponding DSA in the serum. Interestingly in one patient (p#9), while only 1 circulating DSA (DR11:01) was detected, the B-cell Elispot revealed the presence of an additional alloreactive d-s ASC clone circulating in peripheral blood that had been previously observed in the circulation (DR11:01 and also A24:02).

The assessment of d-s ASC responses prior to transplantation could be performed in 10/16 patients developing ABMR. In addition, 7 highly sensitized (patients #17 to #23) as well as 7 non-sensitized (patients #24 to #30) transplants not developing ABMR were also evaluated for the presence of d-s ASC frequencies prior to transplantation. As displayed in FIG. 13B, most patients developing ABMR did not show the corresponding DSA in the serum prior to transplantation, whereas the majority of them showed detectable d-s HLA-ASC frequencies in the periphery. Remarkably, as shown in table 3, patients with preformed d-s ASC responses, showed obvious features of previous allogeneic sensitization. To note, the only patient without detectable pre-transplant d-s ASC responses and no DSA (p#4), did not show previous patterns of HLA sensitization. Conversely, circulating DSA and d-s HLA-ASC frequencies were not detected prior to transplantation in non-sensitized as well as in most highly HLA-sensitized individuals not developing early ABMR (0/7 vs 1/7 vs 9/10, $p<0.001$). Surprisingly, one highly sensitized patient (#17) having received one previous kidney allograft showed detectable pre-transplant d-s ASC against 1 evaluated donor HLA mismatch antigen.

In addition, when the supernatant of expanded alloreactive memory B cells was tested for its donor-specificity using flow-cytometry analysis, positives B and T-cell flow cross-match tests were obtained.

TABLE 3

Evaluation of donor HLA-sp IgG-ASC frequencies

| Patient | Recipient HLA type and Donor HLA types | HLA-Ag (DSA) | Number Previous TX | Highest pre-TX PRA (%) | DSA at any time prior to TX (MFI) | DSA harbored in previous TX | On-going ABMR Ab MFI | On-going ABMR HLA-sp BCE (ratio) | Pre-TX Ab MFI | Pre-TX HLA-sp BCE (ratio) |
|---|---|---|---|---|---|---|---|---|---|---|
| \multicolumn{11}{l}{Highly HLA-sensitized kidney transplant patients developing early ABMR after transplantation} | | | | | | | | | | |
| Pat#1 | R: A02 A24; B07 B15; DR01 DR13 D: A11 A32; B47 B60; DR01 DR13 | A11:01 | 1 | 29 | Yes (5289) | Yes | 4929 | 0.15 | 5289 | 0.26 |
| Pat#2 | R: A29 A69; B35 B44; DR07 DR11 cD: A02 A24; B18 B51; DR03 DR4 | A24:02 | 1 | 90 | No (250) | No | 2039 | 0.45 | 483 | 0.30 |
| Pat#3 | R: A02 A24; B35 B60; DR14 DR13 cD: A11 A32; B47 B60; DR01 DR13 | A11:01 | 1 | 62 | Yes (11652) | No | 9644 | 0.30 | 747 | 0.12 |
| Pat#4 | R: A03 A34; B07 B08; DR01 DR03 cD: A02 A03; B08 B18; DR03 DR11 | DR11:01 | 0 | 0 | No (150) | — | 1200 | 0.40 | 200 | 0 |
| Pat#5 | R: A02 A03; B07 B37; DR01 DR15 cD: A23 A24; B07 B44; DR07 DR11 | A24:02 DR11:01 | 3 | 40 | Yes (2480) | No | 2842 3540 | 0.40 0.30 | 100 200 | 040 0.60 |
| Pat#6 | R: A02 A03; B44; DR01 DR15 cD: A01 A03; B44 B45; DR04 DR07 | A01:01 | 1 | 90 | Yes (3001) | Yes | 9093 | 0.65 | 1750 | 0.20 |
| Pat#7 | R: A01 A29; B44 B17; DR03 DR07 cD: A01 A11; B08 B27; DR03 DR01 | A11:01 B27:05 | 3 | 96 | Yes (7255) Yes (18300) | No | 4521 2224 | 0.3 0.27 | 811 148 | 0.2 0.3 |
| Pat#8 | R: A03 A11; B07 B35; DR01 DR15 cD: A02 A33; B14 B35; DR15 DR16 | A02:01 | 1 | 34 | Yes (1959) | No | 1510 | 0.52 | 1959 | 0.54 |
| Pat#9 | R: A32 A33; B37 B38; Dr01 DR10 cD: A24 A31; B35 B39; DR04 DR11 | A24:02 DR11:01 | 1 | 42 | Yes (2255) Yes (11433) | No | 364 4538 | 0.62 0.39 | 67 1391 | 0.617 0.393 |
| Pat#10 | R: A25 A29; B35 B49; DR07- cD: A24 A30; B13 B18; DR01 DR07 | A24:02 | 1 | 77 | Yes (13303) | No | 9545 | 0.8 | 1106 | 0.2 |

TABLE 3-continued

Evaluation of donor HLA-sp IgG-ASC frequencies

| Patient | Recipient HLA type and Donor HLA types | HLA-Ag (DSA) | Number Previous TX | Highest pre-TX PRA (%) | DSA at any time prior to TX (MFI) | DSA harbored in previous TX | On-going ABMR Ab MFI | On-going ABMR HLA-sp BCE (ratio) | Pre-TX Ab MFI | Pre-TX HLA-sp BCE (ratio) |
|---|---|---|---|---|---|---|---|---|---|---|
| Pat#11 | R: A25 A30; B18-; DR15 DR03<br>cD: A02 A33; B14 B18; DR15 DR04 | A02:01 | 0 | 0 | No | — | 6726 | 0.70 | NA | NA |
| Pat#12 | R: A01 A03; B35 B44; DR03 DR04<br>cD: A11 A30; B18 B44; DR03 DR07 | A11:01 | 1 | 25 | NA | No | 2754 | 0.15 | NA | NA |
| Pat#13 | R: A02-; B41 B51; DR13-<br>cD: A02 A24; B07 B51; DR05 DR06 | A24:02 | 0 | 0 | No | — | 8640 | 0.17 | NA | NA |
| Pat#14 | R: A02-, B40 B51; DR08 DR13<br>cD: A02 A11; B15 B52; DR08 DR15 | A11:01 | 1 | 20 | NA | No | 6345 | 0.13 | NA | NA |
| Pat#15 | R: A01 A31; B51 B07; DR11 DR12<br>cD: A01 A03; B07 B56; DR04 DR11 | A03:01 | 1 | 59 | Yes (1850) | No | 14299 | 0.17 | NA | NA |
| Pat#16 | R: A03 A34; B14 B50; DR11 DR14<br>cD: A03 A32; B18 B35; DR30 DR13 | B35:01 | 1 | 61 | Yes (7199) | Yes | 1615 | 0.34 | NA | NA |
| Highly HLA-sensitized kidney transplant patients NOT developing ABMR after transplantation |
| Pat#17 | R: A02 A03; B44-;DR04 DR08<br>cD: A03 A11; *B27* B44; DR04 DR14 | A11:01<br>B27:05 | 1 | 75 | No | No | NAp | NAp | 150<br>1050 | 0.09<br>0.19 |
| Pat#18 | R: A24 A30; B15 B27; DR08 DR11<br>cD: A11-; B15 B38; DR01 DR11 | A11:01 | 1 | 55 | No | No | NAp | NAp | 128 | 0.10 |
| Pat#19 | R: A24 A29; B45 B50; DR04 DR15<br>cD: A01 A31; B08 B45; DR03 DR04 | A01:01 | 0 | 25 | No | — | NAp | NAp | 560 | 0.002 |
| Pat#20 | R: A03 A25; B07 B18; DR04 DR11<br>cD: A11 A29; B35 B49; DR04 DR11 | A11:01 | 1 | 30 | No | No | NAp | NAp | 178 | 0.06 |
| Pat#21 | R: A02 A03; B27 B44; DR04 DR13<br>cD: A02 A68; B51-; DR13- | A68:01 | 0 | 82 | No | — | NAp | NAp | 1503 | 0.10 |
| Pat#22 | R: A03-; B07 B35; DR01 DR15<br>cD: A02 A23; B07 B18; DR01 DR15 | A02:01 | 0 | 64 | No | — | NAp | NAp | 166 | 0.04 |
| Pat#23 | R: A02 A68; B38 B52; DR08 DR13<br>cD: A02 A24; B07 B40; DR08 DR15 | A24:02<br>B07:02 | 0 | 86 | No<br>No | — <br>— | NAp | NAp | 462<br>379 | 0.04<br>0.02 |
| Non HLA-sensitized kidney transplant patients NOT developing ABMR after transplantation |
| Pat#24 | R: A02 A24; B15 B40; DR07 DR11<br>cD: A01 A03; B14 B49; DR07 DR11 | A01:01<br>A03:01 | 0 | 0 | No<br>No | — <br>— | NAp | NAp | Neg* | 0.02<br>0.01 |
| Pat#25 | R: A68- B35 B44; DR11-<br>cD: A01 A32; B35 B40; DR11 DR13 | A01:01 | 0 | 0 | No | — | NAp | NAp | Neg* | 0.06 |
| Pat#26 | R: A02 A24; B38 B51; DR11 DR14<br>cD: A24 A68; B38 B44; DR13 DR14 | A68:01 | 0 | 0 | No | — | NAp | NAp | Neg* | 0.01 |
| Pat#27 | R: A02 A32; B52 B57; DR11 DR15<br>cD: A02 A68; B44 B51; DR04 DR11 | A68:01 | 0 | 0 | No | — | NAp | NAp | Neg* | 0.01 |
| Pat#28 | R: A02 A24; B39 B51; DR13 DR16<br>cD: A02-; B44 B51; DR07 DR11 | DR11:01 | 0 | 0 | No | — | NAp | NAp | Neg* | 0.09 |
| Pat#29 | R: A24 A32; B18 B38; DR01 DR13<br>cD: A02-; B18 B51; DR03 DR09 | A02:01 | 0 | 0 | No | — | NAp | NAp | Neg* | 0.06 |

TABLE 3-continued

Evaluation of donor HLA-sp IgG-ASC frequencies

| Patient | Recipient HLA type and Donor HLA types | HLA-Ag (DSA) | Number Previous TX | Highest pre-TX PRA (%) | DSA at any time prior to TX (MFI) | DSA harbored in previous TX | On-going ABMR Ab MFI | On-going ABMR HLA-sp BCE (ratio) | Pre-TX Ab MFI | Pre-TX HLA-sp BCE (ratio) |
|---|---|---|---|---|---|---|---|---|---|---|
| Pat#30 | R: A02 <u>A24</u>; B38 B44; DR03 DR15<br>cD: A01 <u>A24</u>; B18 B57; DR07 DR11 | A01:01<br>DR11:01 | 0 | 0 | No<br>No | —<br>— | NAp | NAp | Neg* | 0.08<br>0.01 |

Abbreviations: Pat, patient; HLA, Human leucocyte antigens; Ab, antibodies, DSA, donor-specific antibodies, MFI, mean fluorescence intensity; HLA-sp, HLA-specific; BCE, B-cell Elispot; NA, not available. Underlined are displayed donor-recipient matched HLA antigens.
In bold and with an asterisk are shown donor-specific antibodies (DSA).

Figure 14:
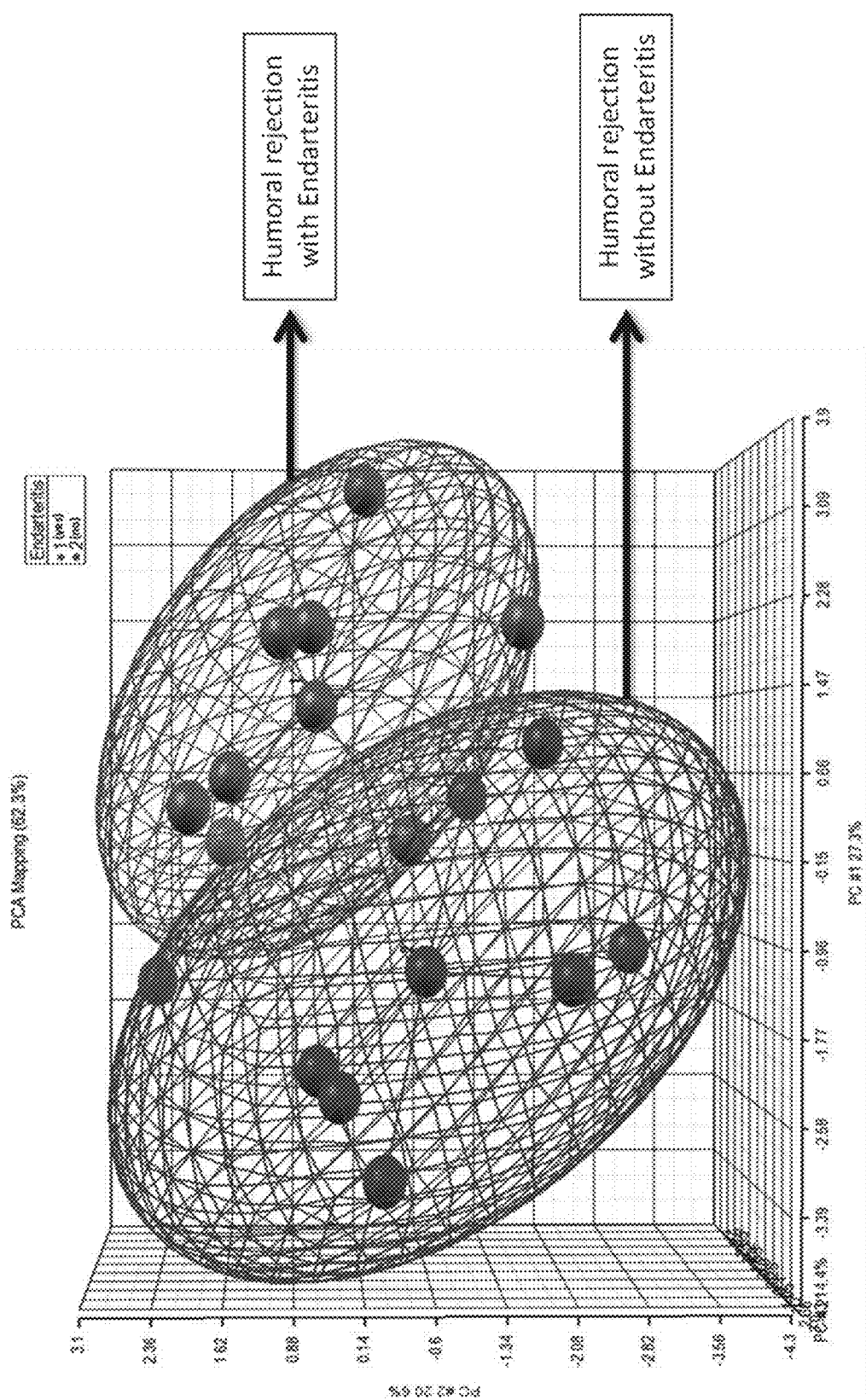
FIG. 14. Principal component analysis (PCA) plot for the presence or absence of endarteritis lesions in patients undergoing ABMR. Each dot represents a patient with respect to the first two principal components: donor-specific memory B-cell alloreactivity (either high or low frequency, defined as higher or lower than 0.35 donor-specific IgG-ASC/polyclonal IgG-ASC ratio) and whether or not the patient experienced endarteritis lesions.

5. High Donor-Specific Memory B-Cell Frequencies is Associated with Severe Vascular ABMR The analysis of the histological Banff scores at the glomeruli, tubuli, interstitium and peritubular capillaries in relation to the strength of the d-s ASC response did not reveal any association between them (data not shown). Conversely, a significantly strong positive correlation was observed between acute vascular lesions (av) and ASC frequencies (r=0.73, p=0.001). An unsupervised principal component analysis (PCA) taking into account the presence of acute vascular lesions and the d-s ASC frequencies, segregated the patients in 2 groups; patients with endarteritis lesions and high d-s ASC responses and those without acute vascular lesions and low d-s ASC responses (PCA mapping=62.3%) (FIG. 14). A sensitivity/specificity ROC curve analysis of d-s ASC frequencies for the prediction of endarteritis, showed that d-s ASC frequencies higher than 0.35 precisely predicted the presence of endarteritis in patients with ABMR (supplementary FIG. 4). Using this cut-off, 7/10 (70%) high ASC-alloreactive patients at the time of ABMR showed endarteritis as compared to only 1/6 (16.6%) low ASC alloreactive patients (p=0.039). Similarly, but pre-transplantation, 5/5 (100%) high d-s alloreactive ASC patients showed endarteritis, whereas only 1/4 (25%) low ASC alloreactives developed endarteritis (p=0.01).

To further investigate whether the strength of the HLA-sp memory alloimmune response had any impact on the type or severity of ABMR, we made an unsupervised principal component analysis taking into account 4 variables: the presence or absence of concomitant acute vascular lesions (av) and the strength of donor HLA-sp IgG-ASC frequencies both before and during acute ABMR (high or low donor-specific IgG-ASC/polyclonal IgG-ASC). Higher donor HLA-sp IgG-ASC/polyclonal IgG-ASC ratios than 0.35 was revealed to precisely predict the advent of endarteritis lesions in patients undergoing ABMR (FIG. 14). As shown in FIG. 14, two different phenotypes were identified: high donor-specific memory B-cell alloreactive patients showed more concomitant acute vascular lesions as compared to patients with lower memory B-cell responses at the time of rejection both before and during acute ABMR (during ABMR: 6/8 high alloreactive patients showed endarteritis as compared to only 1/7 low B-cell alloreactive patients, p=0.019; Pre-transplantation: all 4 high pre-TX anti-donor B-cell alloreactive patients showed endarteritis lesions as compared to only 1/4 low B-cell alloreactive patents, p=0.028).

Figure 15:
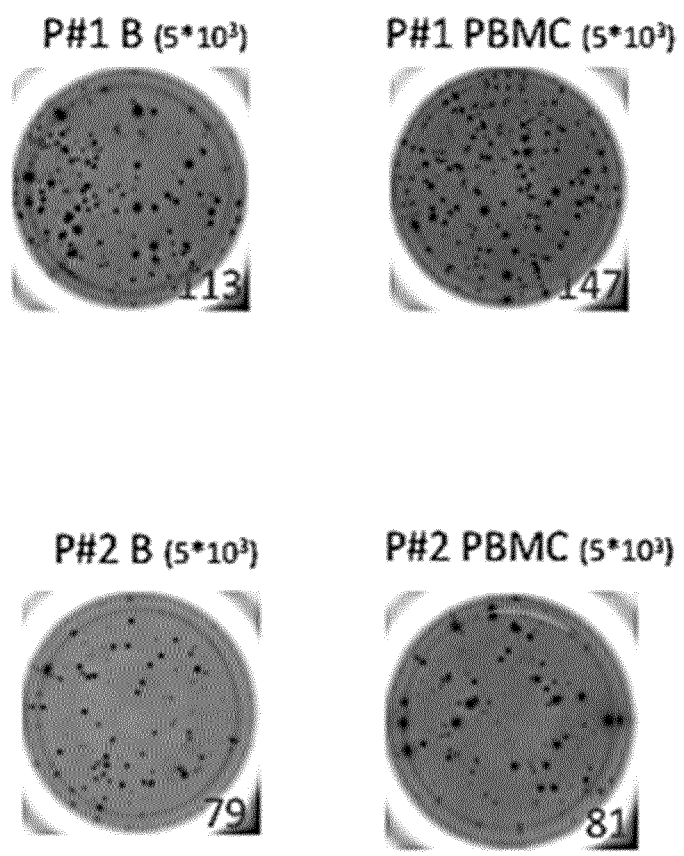
FIG. 15. The stimulation process of circulating memory B cells using the R848 TLR agonist and IL-2 yields to the same amount of antibody-secreting memory B cells (ASC) and HLA-specific IgG-ASC frequencies if using either total Peripheral blood mononuclear cells (PBMCs) or purified B cells. PBMC or purified B cells (with partial depletion of T cells; Heidt S et al Am J Transplant 2012) of two HLA-A02:01 sensitized patients (P#1 and P#2) were stimulated with R848 and IL-2. Results show an equivalent frequency of HLA A02:01-specific IgG-producing ASC was obtained when using either purified B cells or PBMC FIG. 16. Three-day PBMC stimulation using a CD40 monoclonal antibody allows detection of HLA-specific antibody-producing cells. The use of an anti-CD40 monoclonal antibody and IL-2 allows for the differentiation of circulating HLA-specific memory B cells to HLA-specific antibody secreting cells after a 3-day culture. HLA-specific memory B cells capable of producing HLA-specific IgG-antibodies are clearly detected using the HLA B-cell Elispot assay after a 3-day memory B-cell differentiation culture.

Example 4: Stimulation of Circulating Memory B Cells Using Peripheral Blood Mononuclear Cells or Purified B Cells The stimulation process of circulating memory B cells using the R848 TLR agonist and IL-2 yields the same amount of ASCs and HLA-specific IgG-ASC frequencies when using either total peripheral blood mononuclear cells (PBMCs) or purified B cells. B cells were purified as described elsewhere (Heidt et al., 2012, cited supra), with partial depletion of T cells, and subsequently stimulated using the R848 TLR agonist and IL-2 as described above. Table 4 and FIG. 15 show results obtained with PBMC or purified B cells of two HLA-A02:01 sensitized patients (P#1 and P#2) stimulated with R848 and IL-2. As shown, a very similar percentage of ASC (Table 4) as well as equivalent frequency of HLA A02:01-specific IgG-producing ASC (FIG. 15) was obtained when using either purified B cells or PBMC.

TABLE 4

Yields of ASC following stimulation of purified B cells or PBMC with R848 and IL2

| Type of cellular stimulation | Patients | Cell source for the stimulation | Percentage of ASC (CD20$^{low}$CD27$^+$CD38$^{++}$IgD$^-$/ B cells (CD19$^+$)) |
|---|---|---|---|
| R848 + IL2 | Patient #1 | Purified B cells | 0.61% |
| | | PBMC | 0.55% |
| | Patient #2 | Purified B cells | 0.84% |
| | | PBMC | 0.82% |

Example 5: Multiple Detection of HLA Antibody Specificities in a Single Well

Different fluorochrome-labeled multimerized HLA molecules were used in a multiplex assay for the detection of HLA-specific memory B cells capable of producing HLA-specific antibodies with different specificities in a single ELISPOT well. The following protocol was developed for this multiplex assay:

5.1. Sample Preparation (Day 0)
1. Isolate PBMCs by density gradient centrifugation (Ficoll-Pâque) and resuspend cells in complete medium, RPMI++. 2. Count cells by hematocytometer.
3. Adjust cell concentration to $1.5 \times 10^6$ in 1 ml complete medium in a 15 ml falcon tube with a filter vented cap.
4. Add R848 1 ug/ml, IL-2 10 ng/ml.
5. Incubate at 37° C. with 5% $CO_2$ for 6 days.

5.2. Plate Coating (Day 5)
1. Dilute the coating anti IgG mAbs to 15 ug/ml sterile PBS PH 7.4.
2. Remove the Elispot plates (type S5EJ104107 and MAIPSWU10) from the package and pre-wet with 50 ul 70% ethanol per well for maximum 2 minutes.

3. Wash plate×5 with 200 ul/well sterile water. Do not allow the plate to dry out during this process. if so repeat the pre-wetting step.
4. Add 100 ul/well of the antibody solution 15 ul/ml.
5. Incubate plate overnight at 4° C.
5.3. Plate Seeding (Day 6)
1. Wash plate×5 with 200 ul/well with sterile PBS, to remove excess antibody.
2. Block plate by adding 200 ul/well complete medium (RPMI++).
3. Incubate for 1 h at room temperature.
4. Wash plate with 200 ul/well PBS.
5. Wash cells from incubator tubes extensively with RPMI++. (make sure there is no supernatant left).
6. Count cells and adjust to adequate concentration.
7. Seed 4.500 cells/well per duplicate on the non-fluorescent IgG coated plate for the total IgG determination.
8. Seed 450.000 cells/well per duplicate on the fluorescent IgG coated plate for the HLA-specific IgG detection.
9. Jacket plates in aluminium foil and incubate for 20 h at 37° C. in a $CO_2$ incubator.
5.4 Detection of Spots
1. Total IgG spot detection. Prepare solution of biotin-labeled antibody 1 ug/ml PBS.
2. Antigen-specific IgG spot detection. Dilute HLA-Dextramer to 100 ng/ml. (4 ul dextramer/100 ul PBS).
3. Empty the plate to remove cells and wash 5×200 ul/well PBS.
4. Add 100 ul of biotin-labeled antibody solution to each well.
5. Add 100 ul of FITC-HLA-Dextramer solution to each well.
6. Wrap both plates in aluminium foil and incubate at RT for 2-4 hours.
7. Wash the plates 5 times with PBS.
9. Add 100 ul streptavidin-ALP diluted 1:1000 in PBS, to each total IgG well.
10. Incubate both plates for 1 h at room temperature.
11. Add 100 ul of PE-HLA-Dextramer solution to each well.
12. Wrap both plates in aluminium foil and incubate at RT for 2-4 hours.
13. Wash the plates 5 times with PBS.
14. Filtrate BCIP solution (0.45 um). (use it at room temperature).
15. Add 100 ul of BCIP substrate solution per well onto total IgG plate.
16. Add 100 ul of Enhancer per well onto Fluorescent HLA-IgG plate.
17. Incubate for 10 minutes at room temperature.
18. Incubate for 15 minutes at room temperature.
19. Dry plate overnight in the dark and count spots in Bioreader.

In an assay, two different fluorochrome-labeled HLA-dextramers were used to enumerate the presence of both A02:01 and DR11:01-specific antibody-producing cells in a single Elispot well. FITC and PE fluorochromes were used to detect the different HLA-sp memory B-cell clones in a single well (data not shown).

Figure 16:
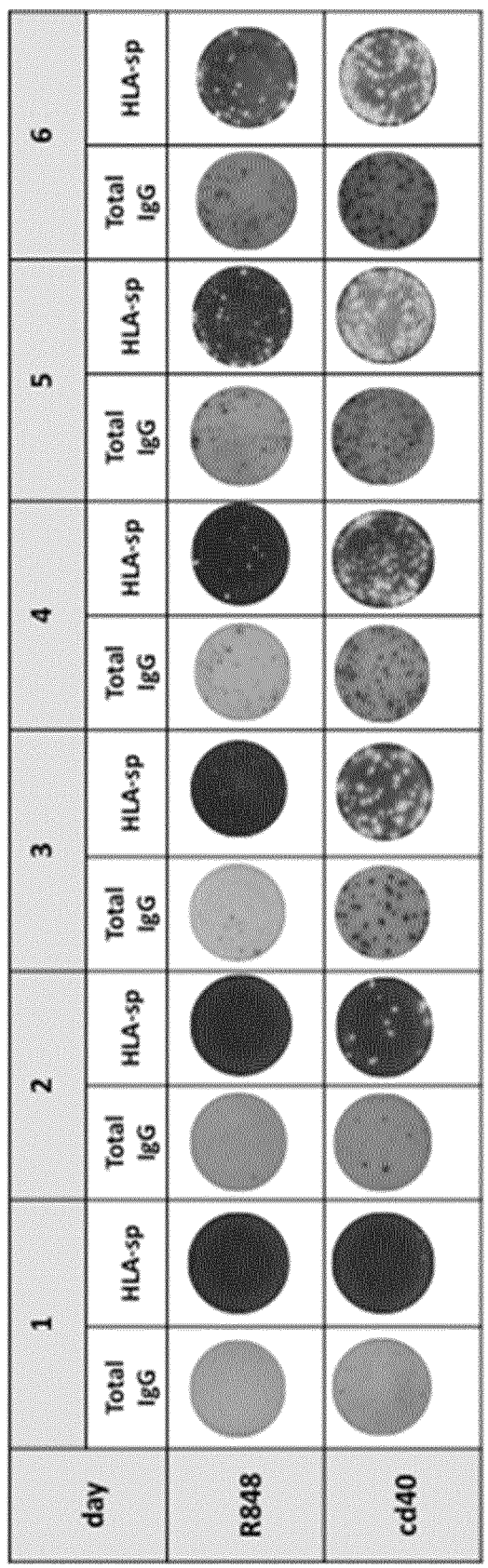

Example 6: Stimulation of PBMCs with IL-2 and a CD40 MAb Allows Detection of HLA-Specific Antibody-Producing Cells The use of an anti-CD40 monoclonal antibody (Clone #82111, R&D systems, Minneapolis, MB, USA), instead of R848, and IL-2 allows the differentiation of circulating HLA-specific memory B cells to HLA-specific antibody secreting cells after a 3-day culture. FIG. 16 shows HLA-specific memory B cells capable of producing HLA-specific IgG-antibodies are clearly detected using the HLA B-cell Elispot assay after a 3-day memory B-cell differentiation culture.

The invention claimed is:

1. An in vitro method for detecting antibody-secreting B cells specific for at least an HLA in a subject comprising:
   i) stimulating memory B cells in a sample of peripheral blood mononuclear cells (PBMCs) containing memory B cells from said subject,
   ii) capturing the antibodies secreted by the stimulated memory B cell of step (i) with an antibody specific to IgG or IgM,
   iii) contacting the antibodies captured in step (ii) with at least an HLA multimer of said HLA wherein the HLA multimer is a polymeric molecule to which a plurality of molecules of said HLA is attached and
   iv) detecting the HLA multimer of said HLA bound to the antibodies captured in step (ii).

2. The in vitro method according to claim 1, wherein the value obtained in step (iv) is normalized to the level of total antibodies present in the sample.

3. The in vitro method according claim 1, wherein the stimulating step (i) is carried out by incubating the sample containing B cells in the presence of IL-2 and at least one compound selected from a TLR agonist and an anti-CD40 antibody.

4. The in vitro method according to claim 3 wherein the TLR agonist is a TLR-7/8 agonist.

5. The in vitro method according to claim 4, wherein the TLR-7/8 agonist is R848.

6. The in vitro method according to claim 1, wherein the antibody specific to IgG or IgM is immobilised onto a solid surface.

7. The in vitro method according to claim 1, wherein the sample is a peripheral blood sample containing peripheral blood mononuclear cells (PBMCs).

8. The in vitro method according to claim 1, wherein the polymeric molecule is a dextran.

9. The in vitro method according to claim 1, wherein a label is attached to the HLA multimer.

10. The in vitro method according to claim 1, wherein the antibodies captured in step (ii) are contacted in step (iii) with at least two HLA multimers, wherein the type of HLA molecules contained in each of said at least two HLA multimer is different.

11. The in vitro method according to claim 10, wherein a different label is attached to each of the at least two HLA multimers.

12. The in vitro method according to claim 9, wherein the label is a fluorochrome molecule.

13. The in vitro method according to claim 12, wherein the fluorochrome molecule is selected from fluorescein isothiocyanate (FITC), Phycoerythrin, and R-Phycoerythrin (PE).

14. An in vitro method for determining the risk of a subject of having humoral rejection after allogeneic organ or tissue transplant, comprising detecting in a sample from said subject the levels of antibody-secreting B cells specific for at least an HLA using the method of claim 1, wherein said HLA is present in the transplanted organ or tissue or in the organ or tissue to be transplanted and wherein increased levels of antibody-secreting B cells specific for said HLA in relation to a reference value are indicative of said subject having a high risk of humoral rejection.

15. An in vitro method for determining the risk of a subject of suffering endarteritis associated with post-transplant humoral rejection after allogeneic organ or tissue transplant, comprising detecting in a sample from said subject the levels of antibody-secreting B cells specific for at least an HLA using the method of claim 1, wherein said HLA is present in the transplanted organ or tissue or in the organ or tissue to be transplanted and wherein increased levels of antibody-secreting B cells specific for said HLA in relation to a reference value are indicative of said subject having a high risk of suffering endarteritis associated with post-transplant humoral rejection.

16. An in vitro method for selecting a subject to receive an allogeneic organ or tissue transplant comprising detecting in a sample from said subject the levels of antibody-secreting B cells specific for at least an HLA using the method of claim 1, wherein said HLA is present in the organ or tissue to be transplanted and wherein the subject is selected to receive said allogeneic organ or tissue transplant if decreased levels of antibody-secreting B cells specific for said HLA in relation to a reference value are detected.

17. The in vitro method according to claim 14, wherein the organ transplant is kidney transplant.

18. An in vitro method for determining the presence of humoral sensitization against at least an HLA in a subject comprising detecting the levels of antibody-secreting B cells specific for said HLA using the method of claim 1, wherein the detection of an antibody-secreting B cell specific for said HLA is indicative of said subject having a humoral sensitization against said HLA.

19. The in vitro method according to claim 18, wherein if an antibody-secreting B cell specific for said HLA is detected, the method additionally comprises a step of correlating the levels of antibody-secreting B cells specific for said HLA or the ratio of antibody-secreting B cells specific for at least said HLA over total antibody-secreting B cells with a degree of humoral sensitization.

* * * * *